United States Patent
Ozaki

(10) Patent No.: US 10,280,440 B2
(45) Date of Patent: May 7, 2019

(54) METHOD OF PRODUCING LIPID USING ACYL-ACP THIOESTERASE

(71) Applicant: Kao Corporation, Chuo-ku, Tokyo (JP)

(72) Inventor: Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/520,138

(22) PCT Filed: Nov. 6, 2015

(86) PCT No.: PCT/JP2015/081356
§ 371 (c)(1),
(2) Date: Apr. 19, 2017

(87) PCT Pub. No.: WO2016/076231
PCT Pub. Date: May 19, 2016

(65) Prior Publication Data
US 2017/0335354 A1 Nov. 23, 2017

(30) Foreign Application Priority Data
Nov. 14, 2014 (JP) ................ 2014-231355

(51) Int. Cl.
*C12N 5/10* (2006.01)
*C12N 9/16* (2006.01)
*C12P 7/64* (2006.01)

(52) U.S. Cl.
CPC ............. *C12P 7/6409* (2013.01); *C12N 5/10* (2013.01); *C12N 9/16* (2013.01); *C12P 7/64* (2013.01); *C12P 7/6436* (2013.01); *C12Y 301/02* (2013.01); *C12Y 301/02014* (2013.01)

(58) Field of Classification Search
None
See application file for complete search history.

(56) References Cited

U.S. PATENT DOCUMENTS

| 2015/0307860 A1 | 10/2015 | Ozaki et al. |
| 2017/0044580 A1 | 2/2017 | Shgihara et al. |

FOREIGN PATENT DOCUMENTS

| JP | 2015-177771 A | 10/2015 |
| WO | WO 92/20236 A1 | 11/1992 |
| WO | WO 2014/103930 A1 | 7/2014 |
| WO | WO 2015/133305 A1 | 9/2015 |
| WO | WO 2015/194628 A1 | 12/2015 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
International Search Report (ISR) for PCT/JP2015/081356; I.A. fd: Nov. 6, 2015, dated Feb. 16, 2016 from the Japan Patent Office, Tokyo, Japan.
International Preliminary Report on Patentability (IPRP), Chapter I of the Patent Cooperation Treaty, including the Written Opinion for PCT/JP2015/081356; I.A. fd: Nov. 6, 2015, dated May 16, 2017, by the International Bureau of WIPO, Geneva, Switzerland.
Radakovits, R. et al., 4-hydroxybenzoyl-thioesterase family active site protein [Nannochloropsis gaditana CCMP526], [online], NCBI Reference Sequence: XP_005853517.1, Oct. 28, 2013, [retrieval date Feb. 4, 2016], Internet<URL: http://www.ncbi.nlm.nih.gov/protein/553181119?sat=21&satkey=8186544>.
Radakovits, R. et al., "Draft genome sequence and genetic transformation of the oleaginous alga *Nannochloropis gaditana*," Nat Commun. Feb. 21, 2012;3:686. doi: 10.1038/ncomms1688, Nature Publishing Group, London, England.
Gong, Y. et al., "Characterization of a novel thioesterase (PtTE) from *Phaeodactylum tricornutum*,"J Basic Microbiol. Dec. 2011;51(6):666-72. doi: 10.1002/jobm.201000520. Epub Jun. 9, 2011, Wiley-VCH Verlag, Weinheim, Germany.
Voekler, TA, et al., "Fatty acid biosynthesis redirected to medium chains in transgenic oilseed plants," Science. Jul. 3, 1992;257(5066):72-74, Am. Assoc. Adv. Sci, Washington, DC.
Excerpted file history, U.S. Appl. No. 14/646,895: non-final rejection dated Feb. 13, 2017 and Preliminary Amendment filed May 22, 2015, downloaded Apr. 27, 2017, USPTO, Alexandria, VA.

* cited by examiner

*Primary Examiner* — Iqbal H Chowdhury
(74) *Attorney, Agent, or Firm* — Sterne, Kessler, Goldstein & Fox P.L.L.C.

(57) ABSTRACT

[Problems] To provide a method of producing a lipid, containing enhancing productivity of medium chain fatty acids or the lipid containing these medium chain fatty acids as components.
[Means to solve] A method of producing a lipid, containing the steps of:
culturing a transformant in which a gene encoding any one of the following proteins (A) to (C) is introduced into a host, and
collecting a lipid from the cultured product:
(A) a protein consisting of the amino acid sequence of the 91st to 348th positions set forth in SEQ ID NO: 1;
(B) a protein consisting of an amino acid sequence having 80% or more identity with the amino acid sequence of the 91st to 348th positions set forth in SEQ ID NO: 1, and having acyl-ACP thioesterase activity; and
(C) a protein containing the amino acid sequence of the protein (A) or (B), and having acyl-ACP thioesterase activity.

20 Claims, No Drawings
Specification includes a Sequence Listing.

METHOD OF PRODUCING LIPID USING ACYL-ACP THIOESTERASE

TECHNICAL FIELD

The present invention relates to a method of producing a lipid using an acyl-ACP thioesterase. Further, the present invention also relates to an acyl-ACP thioesterase, a gene encoding the same, and a transformant obtained by introducing the gene, for use in this method.

BACKGROUND ART

Fatty acids are one of the principal components of lipids. In vivo, fatty acids are bonded to glycerin via an ester bond to form lipids such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkylbenzenesulfonic acid salts and the like are utilized as anionic surfactants. Further, polyoxyalkylene alkyl ethers, alkyl polyglycosides and the like are utilized as nonionic surfactants. These surfactants are used for detergents or disinfectants. Other higher alcohol derivatives, such as alkylamine salts and mono- or dialkyl-quaternary amine salts are commonly used for fiber treatment agents, hair conditioning agents or disinfectants. Further, benzalkonium type quaternary ammonium salts are commonly used for disinfectants or antiseptics. Furthermore, higher alcohols having approximately 18 carbon atoms are also useful as a growth promoter for a plant.

Fatty acids and lipids are widely used for various applications shown above, and therefore, it has been attempted to enhance the productivity of fatty acids or lipids in vivo by using plants and the like. Furthermore, the applications and usefulness of fatty adds depend on the number of carbon atoms. Therefore, controlling of the number of carbon atoms of the fatty acids, namely, a chain length thereof has also been attempted.

For example, a method of accumulating fatty acids having 12 carbon atoms by introducing an acyl-ACP thioesterase derived from *Umbellularia californica* (California bay) (Patent Literature 1, and Non-Patent Literature 1) has been proposed.

Recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, the algae are also reported to the effect that the algae have higher lipid productivity and accumulation ability in comparison with plants.

Research has started on a lipid synthesis mechanism of the algae and lipid production technologies utilizing the mechanism, but unclear parts remain in many respects. For example, almost no report has been made so far on the above-mentioned acyl-ACP thioesterase derived from algae, either, and only limited examples of reports are made on genus *Nannochloropsis* or the like (for example, Patent Literature 2).

CITATION LIST

Patent Literatures

Patent Literature 1: WO 92/20236
Patent Literature 2: WO 2014/103930

Non-Patent Literatures

Non-Patent literature 1: Voelker T A, et al., Science, 1992, vol. 257(5066), p. 72-74.

SUMMARY OF INVENTION

The present invention relates to a method of producing a lipid, containing the steps of:
culturing a transformant in which a gene encoding any one of the following proteins (A) to (C) is introduced into a host, and
collecting a lipid from the cultured product:
(A) a protein consisting of the amino acid sequence of the 91st to 348th positions set forth in SEQ ID NO: 1;
(B) a protein consisting of an amino acid sequence having 80% or more identity with the amino acid sequence of the 91st to 348th positions set forth in SEQ ID NO: 1, and having acyl-ACP thioesterase activity; and
(C) a protein containing the amino acid sequence of the protein (A) or (B), and having acyl-ACP thioesterase activity.

The present invention relates to the proteins (A) to (C) (hereinafter, referred to as "the protein of the present invention" or "the acyl-ACP thioesterase of the present invention").

Further, the present invention relates to a gene encoding any one of the proteins (A) to (C) (hereinafter, referred to as "the gene of the present invention").

Furthermore, the present invention relates to a transformant, which is obtained by introducing a gene encoding any one of the proteins (A) to (C) into a host.

Other and further features and advantages of the invention will appear more fully from the following description.

MODE FOR CARRYING OUT THE INVENTION

The present invention is contemplated for providing a method of producing a lipid using an acyl-ACP thioesterase derived from algae, containing enhancing productivity of medium chain fatty acids or the lipid containing these fatty acids as components.

Further, the present invention is contemplated for providing a novel acyl-ACP thioesterase derived from algae and a gene encoding this, which can be suitably used for the method.

Furthermore, the present invention is contemplated for providing a transformant in which the expression of the gene is promoted and productivity of a lipid or fatty acid composition is changed.

The present inventor conducted research on novel acyl-ACP thioesterases derived from algae. As a result, the present inventor found a novel acyl-ACP thioesterase and an acyl-ACP thioesterase gene encoding this from an alga belonging to the genus *Nannochloropsis*. Further, as a result of conducting transformation by using the acyl-ACP thioesterase gene, the present inventor found that, in transformants, the ratio of the content of specific fatty acids to total fatty acid components in the lipid is significantly improved.

The present invention was completed based on these findings.

The present invention can provide a novel acyl-ACP thioesterase, a gene encoding this, and a transformant in which the gene is introduced. A method of producing a lipid using the transformant according to the present invention is excellent in productivity of medium chain fatty acids or the lipid containing these fatty acids as components. In particular, a method of producing a lipid according to the present invention is excellent in productivity of the fatty acids having 8 to 16 carbon atoms, preferably 12 to 16 carbon atoms, more preferably 12 to 14 carbon atoms, further preferably 12 or 14 carbon atoms, and furthermore preferably 14 carbon atoms, and the lipid containing these fatty acids as components.

The acyl-ACP thioesterase, the gene encoding this acyl-ACP thioesterase, the transformant and the method of producing a lipid of the present invention can be suitably used for the industrial production of fatty acids or lipids.

In the present invention, the term "lipid(s)" covers simple lipids, complex lipids and derived lipids. Specifically, "lipid(s)" covers fatty acids, aliphatic alcohols, hydrocarbons (such as alkanes), neutral lipids (such as triacylglycerol), wax, ceramides, phospholipids, glycolipids, sulfolipids and the like.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and amino acid sequence is calculated through the Lipman-Pearson method (see Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell, Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 18 hours.

In the present specification, any numerical expressions in a style of " . . . to . . . " will be used to indicate a range including the lower and upper limits represented by the numerals given before and after "to", respectively.

Furthermore, in the present specification, the term "medium chain" means that the number of carbon atoms of the fatty acid or the fatty acid residue is 8 or more and 16 or less.

Hereinafter, the acyl-ACP thioesterase, the transformant using the same, and the method of producing a lipid of the present invention are described below in order.

1. Acyl-ACP Thioesterase

The protein of the present invention includes a protein having at least amino acid sequence of the 91st to 348th positions in the amino acid sequence set forth in SEQ ID NO: 1, and a protein functionally equivalent to the protein.

The acyl-ACP (acyl carrier protein) thioesterase is an enzyme involved in the biosynthesis pathway of fatty acids and derivatives thereof (such as triacylglycerol (triglyceride)). This enzyme hydrolyzes a thioester bond of an acyl-ACP to form a free fatty acid in a plastid such as a chloroplast of plant and alga or in a cytoplasm of bacteria, fungus and animal. The acyl-ACP is a composite composed of an acyl group (fatty acid residue) and an acyl carrier protein, and is an intermediate in the process of fatty acid biosynthesis. The function of the acyl-ACP thioesterase terminates the synthesis of the fatty acid on the ACP, and then the thus-produced free fatty acids are supplied to the synthesis of triacylglycerol and the like.

To date, several acyl-ACP thioesterases having different reaction specificities depending on the number of carbon atoms and the number of unsaturated bonds of the acyl group (fatty acid residue) of the acyl-ACP substrate are identified. Therefore, acyl-ACP thioesterase is considered to be an important factor in determining the fatty acid composition in vivo.

The "acyl-ACP thioesterase activity" in the present invention means an activity of hydrolyzing the thioester bond of the acyl-ACP.

Specific examples of the protein of the present invention include the following proteins (A) to (C).

(A) A protein consisting of the amino acid sequence of the 91st to 348th positions set forth in SEQ ID NO: 1.
(B) A protein consisting of an amino acid sequence having 80% or more identity with the amino acid sequence of the 91st to 348th positions set forth in SEQ ID NO: 1, and having acyl-ACP thioesterase activity.
(C) A protein containing the amino acid sequence of the protein (A) or (B), and having acyl-ACP thioesterase activity.

The amino acid sequence set forth in SEQ ID NO: 1 is an amino acid sequence of the acyl-ACP thioesterase (hereinafter, also abbreviated as "NoTE2") derived from *Nannochloropsis oculata*, which is an alga belonging to the genus *Nannochloropsis*.

The present inventor found that the region of the 91st to 348th positions in the amino acid sequence set forth in SEQ ID NO: 1 is an important for acting the acyl-ACP thioesterase, and sufficient region for exhibiting the acyl-ACP thioesterase activity. That is, the protein consisting of the amino acid sequence of the 91st to 348th positions set forth in SEQ ID NO: 1 and a protein consisting of an amino acid sequence containing the sequence have the acyl-ACP thioesterase activity.

The protein (A) has a region sufficient for this acyl-ACP thioesterase activity, and acts as the acyl-ACP thioesterase.

The protein (B) consists of an amino add sequence having 80% or more identity with the amino acid sequence of the 91st to 348th positions set forth in SEQ ID NO: 1, and has acyl-ACP thioesterase activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the acyl-ACP thioesterase activity is kept and a part of the amino acid sequence is subjected to mutation.

From the viewpoints of acyl-ACP thioesterase activity, the protein (B) has preferably 88% or more identity, more preferably 90% or more identity, further preferably 95% or more identity, furthermore preferably 96% or more identity, furthermore preferably 97% or more identify, furthermore preferably 98% or more identity, and furthermore preferably 99% or more identity, with the amino acid sequence of the 91st to 348th positions set forth in SEQ ID NO: 1.

Further, with respect to the protein (B), specific examples of the amino acid sequence having 80% or more identity with the amino acid sequence of the 91st to 348th positions set forth in SEQ ID NO: 1 include an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 8 or less amino acids, furthermore preferably 1 or more and 5 or less amino acids, furthermore preferably 1 or more and 4 or less amino acids, furthermore preferably 1 or more and 3 or less amino acids, and furthermore preferably 1 or 2 amino acids, are deleted, substituted, inserted or added in the amino acid sequence of the 91st to 348th positions set forth in SEQ ID NO: 1.

A method of introducing the mutation such as deletion, substitution, insertion or addition into an amino acid sequence includes a method of, for example, introducing a mutation into a nucleotide sequence encoding the amino acid sequence. The method of introducing a mutation into a nucleotide sequence is described later.

The protein (C) contains the amino acid sequence of the protein (A) or (B) as a part of the amino acid sequence of the protein (C), and exhibits acyl-ACP thioesterase activity. The protein (C) may include a sequence other than the amino acid sequence of the protein (A) or (B).

Specific examples of the sequence other than the amino acid sequence of the protein (A) or (B) in the amino acid sequence that constitutes the protein (C) include an arbitrary amino acid sequence other than the 91st to 348th positions set forth in SEQ ID NO: 1, an amino acid sequence having 80% or more identity, preferably 86% or more identity, more preferably 90% or more identity, further preferably 95% or more identify, furthermore preferably 98% or more identity, furthermore preferably 97% or more identity, furthermore preferably 98% or more identity, and furthermore preferably 99% or more identity, with the arbitrary amino acid sequence other than the 91st to 348th positions set forth in SEQ ID NO: 1, or an amino acid sequence in which one or several amino acids, preferably 1 or more and 20 or less amino acids, more preferably 1 or more and 15 or less amino acids, further preferably 1 or more and 10 or less amino acids, furthermore preferably 1 or more and 8 or less amino acids, furthermore preferably 1 or more and 5 or less amino acids, furthermore preferably 1 or more and 4 or less amino acids, furthermore preferably 1 or more and 3 or less amino acids, and furthermore preferably 1 or 2 amino acids, are deleted, substituted, inserted or added into these sequences. These sequences are preferably added to the N-terminal side of the amino acid sequence of the protein (A) or (B).

Moreover, the protein (C) also preferably includes a protein consisting of an amino acid sequence formed such that a signal peptide engaging in transport or secretion of the protean is added to the amino acid sequence of the protein (A) or (B). Specific examples of addition of the signal peptide include addition to an N-terminal of chloroplast transit signal peptide.

The protein (C) may be a protein consisting of an amino acid sequence in which amino acids on an N-terminal side are deleted at an arbitrary position of the 1st to 90th positions set forth in SEQ ID NO: 1.

Further, from the viewpoint of the productivity of specific fatty acids, for example medium chain fatty acids, specifically fatty acids having 12 or 14 carbon atoms, the protein (C) is preferably the following proteins (C1) to (C7).

(C1) A protein consisting of the amino acid sequence of the 1st to 348th positions set forth in SEQ ID NO: 1.
(C2) A protein consisting of the amino acid sequence of the 81st to 348th positions set forth in SEQ ID NO: 1.
(C3) A protein consisting of the amino acid sequence of the 71st to 348th positions set forth in SEQ ID NO: 1.
(C4) A protein consisting of the amino acid sequence of the 74th to 348th positions set forth in SEQ ID NO: 1.
(C5) A protein consisting of the amino acid sequence of the 81st to 348th positions set forth in SEQ ID NO: 1.
(C6) A protein consisting of an amino acid sequence having 80% or more identity, preferably 85% or more identity, more preferably 90% or more identity, further preferably 95% or more identity, furthermore preferably 96% or more identity, furthermore preferably 97% or more identity, furthermore preferably 98% or more identity, and furthermore preferably 99% or more identity, with the amino acid sequence of any one of the proteins (C1) to (C5), and having acyl-ACP thioesterase activity.
(C7) A protein consisting of an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 8 or less amino acids, furthermore preferably 1 or more and 5 or less amino acids, furthermore preferably 1 or more and 4 or less amino acids, furthermore preferably 1 or more and 3 or less amino acids, and furthermore preferably 1 or 2 amino acids, are deleted, substituted, inserted or added to the amino acid sequence of any one of the proteins (C1) to (C5), and having acyl-ACP thioesterase activity.

The present inventor confirmed that the proteins (C1) to (C5) have the acyl-ACP thioesterase activity.

The acyl-ACP thioesterase activity of the protein can be confirmed by, for example, introducing a DNA produced by linking the acyl-ACP thioesterase gene to the downstream of a promoter which functions in a host cell such as *Escherichia coli*, into a host cell which lacks a fatty acid degradation system, culturing the thus-obtained cell under the conditions suitable for the expression of the introduced acyl-ACP thioesterase gene, and analyzing any change caused thereby in the fatty acid composition of the host cell or the cultured liquid by using a gas chromatographic analysis or the like.

Alternatively, the acyl-ACP thioesterase activity can be measured by introducing a DNA produced by linking the acyl-ACP thioesterase gene to the downstream of a promoter which functions in a host cell such as *Escherichia coli*, into a host cell, culturing the thus-obtained cell under the conditions suitable for the expression of the introduced acyl-ACP thioesterase gene, and subjecting a disruption liquid of the cell to a reaction which uses acyl-ACPs, as substrates, prepared according to the method of Yuan et al. (Yuan L. et al., Proc. Natl. Acad. Sci. U.S.A., 1995, vol. 92 (23), p. 10639-10643).

There are no particular limitations on the method for obtaining the protein of the present invention, and the protein can be obtained by chemical techniques, genetic engineering techniques or the like that are ordinarily carried out. For example, a natural product-derived protein can be obtained through isolation, purification and the like from *Nannochloropsis oculata*. Furthermore, protein synthesis may be carried out by chemical synthesis, or a recombinant protein may also be produced by gene recombination technologies. In the case of producing a recombinant protein, the acyl-ACP thioesterase gene described below can be used.

Moreover, the algae belonging to the genus *Nannochloropsis* such as *Nannochloropsis oculata* can also be obtained from culture collection such as private or public research institutes. For example, the algae can be obtained from The culture collection of algae at University of Texas at Austin (UTEX), National Institute for Environmental Studies (NIES), National Center for Marine Algae and Microbiota (NCMA, previous name: CCMP), Culture Collection of Algae and Protozoa (CCAP), or Australian National Algae Culture Collection (CSIRO).

2. Acyl-ACP Thioesterase Gene

The acyl-ACP thioesterase gene of the present invention is a gene encoding any one of the proteins (A) to (C).

Examples of the gene encoding any one of the proteins (A) to (C) include a gene consisting of the nucleotide sequence set forth in SEQ ID NO: 2. The nucleotide sequence set forth in SEQ ID NO: 2 is an example of the nucleotide sequence of the gene encoding the acyl-ACP thioesterase derived from *Nannochloropsis oculata*, and encodes the amino acid sequence set forth in SEQ ID NO: 1. Further, the nucleotide sequence of the 271st to 1,044th positions set forth in SEQ ID NO: 2 encodes the amino acid sequence of the 91st to 348th positions set forth in SEQ ID NO: 1. In addition, a nucleotide sequence of the 1,045th to 1,047th positions set forth in SEQ ID NO: 2 is a termination codon, which does not correspond to any amino acids.

Specific examples of the gene encoding any one of the proteins (A) to (C) include a gene consisting of any one of the following DNAs (a) to (c). However, the present invention is not limited thereto.

(a) A DNA consisting of the nucleotide sequence of the 271st to 1,047th positions set forth in SEQ ID NO: 2.

(b) A DNA consisting of a nucleotide sequence having 80% or more identity with the nucleotide sequence of the 271st to 1,047th positions set forth in SEQ ID NO: 2, and encoding a protein having acyl-ACP thioesterase activity.

(c) A DNA containing the nucleotide sequence of the DNA (a) or (b), and encoding a protein having acyl-ACP thioesterase activity.

From the viewpoints of acyl-ACP thioesterase activity, the DNA (b) has preferably 85% or more identity, more preferably 90% or more identity, further preferably 95% or more identity, furthermore preferably 98% or more identity, furthermore preferably 97% or more identity, furthermore preferably 98% or more identity, and furthermore preferably 99% or more identity, with the nucleotide sequence of the 271st to 1,047th positions set forth in SEQ ID NO: 2.

Further, with respect to the DNA (b), specific examples of the nucleotide sequence having 80% or more identity with the nucleotide sequence of the 271st to 1,047th positions set forth in SEQ ID NO: 2 include a nucleotide sequence in which 1 or several nucleotides, preferably 1 or more and 20 or less nucleotides, more preferably 1 or more and 15 or less nucleotides, further preferably 1 or more and 10 or less nucleotides, furthermore preferably 1 or more and 8 or less nucleotides, furthermore preferably 1 or more and 5 or less nucleotides, furthermore preferably 1 or more and 4 or less nucleotides, furthermore preferably 1 or more and 3 or less nucleotides, furthermore preferably 1 or 2 nucleotides, are deleted, substituted, inserted or added in the nucleotide sequence of the 271st to 1,047th positions set forth in SEQ ID NO: 2.

A method of introducing the mutation such as deletion, substitution, insertion or addition into a nucleotide sequence includes a method of introducing a site-specific mutation, for example. Specific examples of the method of introducing the site-specific mutation include a method of utilizing the Splicing overlap extension (SOE) PCR (Horton et al., Gene, 1989, vol. 77, p. 61-68), the ODA method (Hashimoto-Gotoh et al., Gene, 1995, vol. 152, p. 271-276), and the Kunkel method (Kunkel, T. A., Proc. Natl Acad. Sci. USA, 1985, vol. 82, p. 488). Further, commercially available kits such as Site-Directed Mutagenesis System Mutan-SuperExpress Km kit (manufactured by Takara Bio), Transformer TM Site-Directed Mutagenesis kit (manufactured by Clonetech Laboratories), and KOD-Plus-Mutagenesis Kit (manufactured by Toyobo) can also be utilized. Furthermore, a gene containing a desired mutation can also be obtained by introducing a genetic mutation at random, and then performing an evaluation of the enzyme activities and a gene analysis thereof by an appropriate method.

Furthermore, the DNA (b) is also preferably a DNA capable of hybridizing with a DNA consisting of a nucleotide sequence complementary with the DNA (a) under a stringent condition, and encoding a protein having acyl-ACP thioesterase activity.

The DNA (c) contains the nucleotide sequence of the DNA (a) or (b) as a part of the nucleotide sequence of the DNA (c), and encodes a protein having acyl-ACP thioesterase activity. The DNA (c) may include a sequence other than the nucleotide sequence of the DNA (a) or (b).

Specific examples of the sequence other than the nucleotide sequence of the DNA (a) or (b) in the nucleotide sequence of the DNA (c) include an arbitrary nucleotide sequence other than the 271st to 1,047th positions set forth in SEQ ID NO: 2, a nucleotide sequence having 80% or more identity, preferably 85% or more identity, more preferably 90% or more identity, further preferably 95% or more identity, furthermore preferably 96% or more identity, furthermore preferably 97% or more identity, furthermore preferably 98% or more identity, and furthermore preferably 99% or more identity, with the arbitrary nucleotide sequence other than the 271st to 1,047th positions set forth in SEQ ID NO: 2, or a nucleotide sequence in which one or several nucleotides, preferably 1 or more and 20 or less nucleotides, more preferably 1 or more and 15 or less nucleotides, further preferably 1 or more and 10 or less nucleotides, furthermore preferably 1 or more and 8 or less nucleotides, furthermore preferably 1 or more and 5 or less nucleotides, furthermore preferably 1 or more and 4 or less nucleotides, furthermore preferably 1 or more and 3 or less nucleotides, and furthermore preferably 1 or 2 nucleotides, are deleted, substituted, inserted or added into an arbitrary nucleotide sequence other than the 271st to 1,047th positions set forth in SEQ ID NO: 2.

Moreover, the sequence other than the nucleotide sequence of the DNA (a) or (b) also preferably includes a nucleotide sequence encoding a signal peptide engaging in transport or secretion of the protein. Specific example of the signal peptide includes the proteins described in the protein (C).

These sequences are preferably added to the 5'-terminal side of the nucleotide sequence of the DNA (a) or (b).

The DNA (c) may be a DNA consisting of a nucleotide sequence in which nucleotides on a 5'-terminal side are deleted at an arbitrary position of the 1st to 270th positions set forth in SEQ ID NO: 2.

Further, from the viewpoint of the productivity of specific fatty acids, for example medium chain fatty acids, specifically fatty acids having 12 or 14 carbon atoms, the DNA (c) is preferably the following DNAs (c1) to (c7).

(c1) A DNA consisting of the nucleotide sequence of the 1st to 1047th positions set forth in SEQ ID NO: 2.
(c2) A DNA consisting of the nucleotide sequence of the 181st to 1,047th positions set forth in SEQ ID NO: 2.
(c3) A DNA consisting of the nucleotide sequence of the 211st to 1,047th positions set forth in SEQ ID NO: 2.
(c4) A DNA consisting of the nucleotide sequence of the 220th to 1,047th positions set forth in SEQ ID NO: 2.
(c5) A DNA consisting of the nucleotide sequence of the 241st to 1,047th positions set forth in SEQ ID NO: 2.
(c6) A DNA consisting of a nucleotide sequence having 80% or more identity, preferably 85% or more identity, more preferably 90% or more identity, further preferably 95% or more identity, furthermore preferably 98% or more identity, furthermore preferably 97% or more identity, furthermore preferably 98% or more identity, and furthermore preferably 99% or more identity, with the nucleotide sequence of any one of the DNAs (c1) to (c5), and encoding a protein having acyl-ACP thioesterase activity.
(c7) A DNA consisting of a nucleotide sequence in which 1 or several nucleotides, preferably 1 or more and 20 or less nucleotides, more preferably 1 or more and 15 or less nucleotides, further preferably 1 or more and 10 or less nucleotides, furthermore preferably 1 or more and 8 or less nucleotides, furthermore preferably 1 or more and 5 or less nucleotides, furthermore preferably 1 or more and 4 or less nucleotides, furthermore preferably 1 or more and 3 or less nucleotides, and furthermore preferably 1 or 2 nucleotides, are deleted, substituted, inserted or added to the nucleotide sequence of any one of the DNAs (c1) to (c5), and encoding a protein having acyl-ACP thioesterase activity.

The present inventor confirmed that the gene consisting of any one of the DNAs (c1) to (c5) encodes a protein having acyl-ACP thioesterase activity.

There are no particular limitations on the method for obtaining the acyl-ACP thioesterase gene of the present invention, and the gene can be obtained by genetic engineering techniques that are ordinarily carried out. For example, the gene can be obtained by artificial synthesis based on the amino acid sequence set forth in SEQ ID NO: 1 or the nucleotide sequence set forth in SEQ ID NO: 2. The artificial synthesis of a gene can be achieved by utilizing, for example, the services of Eurofins Genomics or the like. Furthermore, the gene can also be obtained by cloning from *Nannochloropsis oculata*. The cloning can be carried out by, for example, the methods described in Molecular Cloning—A LABORATORY MANUAL THIRD EDITION [Joseph Sambrook, David W. Russell, Cold Spring Harbor Laboratory Press (2001)] or the like.

3. Transformant (1) First Embodiment

The transformant of the first embodiment of the present invention is a transformant in which the expression of a gene encoding any one of the proteins (A) to (C) is promoted.

In the transformant the ability to produce lipids, particularly the ability to produce medium chain fatty acids having 12 to 16 carbon atoms, or lipids containing these medium chain fatty acids as components (productivity of medium chain fatty acids or lipids containing these medium chain fatty acids as components, a ratio of medium chain fatty acids in the total fatty acids to be produced, a ratio of lipids containing medium chain fatty acids as components in the total lipids to be produced) is significantly improved. Moreover, in the transformant, in comparison with a host, the fatty acid composition in the lipid (a ratio of specific fatty acids relative to the total fatty acids to be produced, a ratio of lipids containing specific fatty acids as components in the total lipids to be produced) changes. Therefore, the present invention using the transformant can be preferably applied to production of specific lipids, particularly medium chain fatty acids or lipids containing these medium chain fatty acids as components, preferably fatty acids having 8 or more and 16 or less carbon atoms or lipids containing these fatty acids as components, more preferably fatty acids having 12 or more and 16 or less carbon atoms or lipids containing these fatty acids as components, further preferably fatty acids having 12 or more and 14 or less carbon atoms or lipids containing these fatty acids as components, furthermore preferably fatty acids having 12 or 14 carbon atoms or lipids containing these fatty acids as components, and furthermore preferably fatty acids having 14 carbon atoms or lipids containing these fatty acids as components.

Further, in the transformant of the embodiment, in comparison with a host itself, production efficiency of medium chain fatty acids or lipids containing these medium chain fatty acids as components is significantly improved. Therefore, the present invention using the transformant can be preferably applied to production of the lipid.

The ability to produce fatty acids and lipids of the acyl-ACP thioesterase can be measured by the method used in the Examples. Moreover, in the present specification, a cell in which the expression of a gene encoding an objective protein herein is promoted is also referred to as the "transformant", and a cell in which the expression of the gene encoding the objective protein is not promoted is also referred to as the "host" or "wild type strain".

A method of promoting the expression of the acyl-ACP thioesterase gene can be appropriately selected from an ordinarily method. For example, a method of introducing the acyl-ACP thioesterase gene into a host, and a method of modifying expression regulation regions of the gene (promoter, terminator, or the like) in a host having the acyl-ACP thioesterase gene on a genome, can be selected.

The method of introducing an acyl-ACP thioesterase gene into a host and promoting the expression of the gene is described.

The transformant that can be preferably used in the present invention is obtained by introducing a gene that encodes acyl-ACP thioesterase into a host according to an ordinarily genetic engineering method. Specifically, the transformant can be produced by preparing an expression vector or a gene expression cassette which is capable of expressing a gene that encodes acyl-ACP thioesterase in a host call, introducing this vector or cassette into host cells, and thereby transforming the host cells.

The host for the transformant is not particularly limited, and can be appropriately selected from ordinarily used hosts. For example, microorganisms (including algae and microalgae), plants or animals can be used. Among these, microorganisms or plants are preferable, and microorganisms are more preferable as a host, from the viewpoints of production efficiency and the usability of lipids to be obtained.

As the microorganisms, prokaryotes and eukaryotes can be used. Prokaryotes include microorganisms belonging to the genus *Escherichia*, microorganisms belonging to the genus *Bacillus*, microorganisms belonging to the genus *Synechocystis*, microorganisms belonging to the genus *Synechococcus*, or the like. Eukaryotes include eukaryotic microorganisms belonging to yeast, filamentous fungi or the like. Among these, from the viewpoint of the productivity of lipids, *Escherichia coli* belonging to the genus *Escherichia*, *Bacillus subtle* belonging to the genus *Bacillus*, *Rhodospo-*

*ridium toruloides* belonging to yeast, and *Mortierella* sp. belonging to filamentous fungi are preferable, and *Escherichia coli* is more preferable.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferable, and algae belonging to the genus *Nannochloropsis* are more preferable. Specific examples of the algae belonging to the genus *Nannochloropsis* include *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp. Among these, from the viewpoint of the productivity of lipids, *Nannochloropsis oculata* or *Nannochloropsis gaditana* is preferable, and *Nannochloropsis oculata* is more preferable.

As the plants, from the viewpoint of a high lipid content of seeds, *Arabidopsis thaliana*, rapeseed, *Cocos nucifera*, palm, cuphea or *Jatropha curcas* is preferable, and *Arabidopsis thaliana* is more preferable.

A vector for use as the plasmid vector for gene expression or the gene expression cassette (plasmid) may be any vector capable of introducing the gene encoding the acyl-ACP thioesterase into a host, and expressing the gene in the host call. For example, a vector which has expression regulation regions such as a promoter and a terminator in accordance with the type of the host to be used, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector include, in the case of using a microorganism as the host, pBluescript (pBS) II SK(-) (manufactured by Stratagene), a pSTV-based vector (manufactured by Takara Bio), pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Mckenzie. T. et al., (1986), Plasmid 15(2); p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(-) or pMW218/219 is preferably used.

When the algae are used as the host, specific examples of the vector include pUC19 (manufactured by Takara Bio), P66 (Chlamydomonas Center), P-322 (Chlamydomonas Center), pPha-T1 (see Yangmin Gong, et al., Journal of Basic Microbiology, 2011, vol. 51, p. 666-672) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Oliver Kilian, et al., Proceedings of the National Academy of Sciences of the United States of America, 2011; vol. 108(52), by using the DNA fragment consisting of the gene of the present invention, a promoter and a terminator (gene expression cassette). Specific examples of this DNA fragment include a PCR-amplified DNA fragment and a restriction enzyme-cut DNA fragment.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector is preferably used.

Moreover, a kind of promoter or terminator regulating the expression of the gene encoding an objective protein can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a derivative that can be derived by addition of isopropyl β-D-1-thiogalactopyranoside (IPTG), Rubisco operon (rbc), PSI reaction center protein (psaAB), D1 protein of PSII (psbA), cauliflower mosaic virus 35S RNA promoter, promoters for housekeeping genes (e.g., tubulin promoter, actin promoter and ubiquitin promoter), rapeseed-derived *Napin* gene promoter, plant-derived Rubisco promoter, a promoter of a violaxanthin/(chlorophyll a)-binding protein VCP1 gene derived from the genus *Nannochloropsis* (VCP1 promoter, VCP2 promoter) (Oliver Kilian, et al., Proceedings of the National Academy of Sciences of the United States of America, 2011; vol. 108(2)), and a promoter of a oleosin-like protein LDSP (lipid droplet surface protein) gene derived from the genus *Nannochloropsis* (Astrid Vieler, et al., PLOS Genetics, 2012; vol. 8(11): e1003064. doi: 10.1371).

Moreover, a kind of selection marker for confirming introduction of the gene encoding an objective protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

Introduction of the gene encoding an objective protein to the vector can be constructed by an ordinary technique such as restriction enzyme treatment and ligation. Moreover, upon construction of the expression vector, in addition to the gene encoding the acyl-ACP thioesterase, a sequence useful for translation of the gene, for example, the sequence corresponding to the initiation codon or the termination codon can be appropriately supplemented.

The method for transformation is not particularly limited as long as it is a method capable of introducing a target gene into a host. For example, a method of using calcium ion, a general competent cell transformation method (J. Bacterial. 93, 1925 (1967)), a protoplast transformation method (Mol. Gen. Genet. 168, 111 (1979)), an electroporation method (FEMS Microbiol. Lett. 55, 135 (1990)), or an LP transformation method (T. Akamatsu, et al., Archives of Microbiology, 1987, 146, p. 353-357; T. Akamatsu, et al., Bioscience, Biotechnology, and Biochemistry, 2001, 65, 4, p. 823-829), can be used. When the host is the algae belonging to the genus *Nannochloropsis*, transformation can also be performed by using the electroporation method described in Randor Radakovits, et al., Nature Communications, DOI: 10.1038/ncomms1688. 2012.

The selection of a transformant having a target gene fragment introduced therein can be carried out by utilizing the selection marker or the like. For example, the selection can be carried out by using an indicator whether a transformant acquires the drug resistance as a result of introducing a drug resistance gene derived from a vector into a host cell together with a target DNA fragment upon the transformation. Further, the introduction of a target DNA fragment can also be confirmed by PCR using a genome as a template and the like.

In a host having an acyl-ACP thioesterase gene on a genome, a method of modifying expression regulation regions of the gene and promoting the expression of the gene is described.

The "expression regulation region" indicates the promoter or the terminator, in which these sequences are generally involved in regulation of the expression amount (transcription amount, translation amount) of the gene adjacent thereto. In a host having the above-described acyl-ACP thioesterase gene on a genome, productivity of medium chain fatty acids or lipids containing these medium chain fatty acids as components can be improved by modifying expression regulation regions of the gene and promoting the expression of the acyl-ACP thioesterase gene.

Specific examples of the method of modifying the expression regulation region include interchange of promoters. In the host having the above-mentioned acyl-ACP thioesterase gene on the genome, the expression of the above-described acyl-ACP thioesterase gene can be promoted by interchanging the promoter of the gene (hereinafter, also referred to as "acyl-ACP thioesterase promoter") with a promoter having higher transcriptional activity. For example, in *Nannochloropsis oculata* NIES-2145 strain being one of the hosts having the acyl-ACP thioesterase genes on the genome, the acyl-ACP thioesterase gene exists beneath a DNA sequence consisting of the nucleotide sequence set forth in SEQ ID NO: 37, and a promoter region exists in the DNA sequence consisting of the nucleotide sequence set forth in SEQ ID NO: 37. The expression of the above-described acyl-ACP thioesterase gene can be promoted by partially or wholly interchanging the DNA sequences consisting of the nucleotide sequence set forth in SEQ ID NO: 37 with the promoter having higher transcriptional activity.

The promoter used for interchanging the acyl-ACP thioesterase promoters is not particularly limited, and can be appropriately selected from the promoters that are higher in the transcriptional activity than the acyl-ACP thioesterase promoter and suitable for production of the medium chain fatty acids or the lipids containing these fatty acids as the components.

When the host is *Nannochloropsis*, tubulin promoter, heat shock protein promoter, above-described promoter of a violaxanthin/(chlorophyll a)-binding protein gene (VCP1 promoter, VCP2 promoter), and promoter of a oleosin-like protean LDSP gene derived from the genus *Nannochloropsis*, can be preferably used. From a viewpoint of improvement in the productivity of medium chain fatty acids or lipids containing these medium chain fatty acids as components, promoter of a violaxanthin/(chlorophyll a)-binding protein gene and promoter of LDSP gene are more preferable.

The above-described modification of a promoter can employ according to an ordinarily method such as homologous recombination. Specifically, a linear DNA fragment containing an upstream and downstream regions of a target promoter in a host genome and containing other promoter instead of the target promoter is constructed, and the resultant DNA fragment is incorporated into a host cell to cause double crossover homologous recombination on the side upstream and downstream of the target promoter of the host genome. Then the target promoter on the genome is substituted with other promoter fragment, and the promoter can be modified.

The method of modifying a target promoter using homologous recombination can be conducted with, for example, reference to literature such as Besher et al., Methods in molecular biology, 1995, vol. 47, p. 291-302. In particular, when the host is the algae belonging to the genus *Nannochloropsis*, specific region in a genome can be modified, with referring to literature such as Oliver Kilian, et al., Proceedings of the National Academy of Sciences of the United States of America, 2011, vol. 108(52), by homologous recombination method.

(2) Second Embodiment

The transformant of the second embodiment of the present invention is a transformant in which, in a host cell having the acyl-ACP thioesterase gene of the present invention, the gene is subjected to deletion, mutation or repression of expression. The transformant (hereinafter, also referred to as "transformant of the second embodiment") can be obtained by subjecting to deletion, mutation or repression of expression of a gene encoding any one of the proteins (A) to (C) in the host.

The host of the transformant of the second embodiment only needs to have the acyl-ACP thioesterase gene of the present invention. For example, microorganisms, plants or animals can be used as the host. Among these, microorganisms are preferable, and *Escherichia coli* or microalgae are more preferable, from a viewpoint of the productivity of lipids.

As the microalgae, from a viewpoint of the productivity of lipids, algae belonging to the genus *Nannochloropsis* are preferable. Specific examples of the algae belonging to the genus *Nannochloropsis* include *Nannochloropsis oculata, Nannochloropsis gaditana, Nannochloropsis salina, Nannochloropsis oceanica, Nannochloropsis atomus, Nannochloropsis maculata, Nannochloropsis granulata*, and *Nannochloropsis* sp. Among these, from a viewpoint of the productivity of lipids, *Nannochloropsis oculata* or *Nannochloropsis gaditana* is preferable, and *Nannochloropsis oculata* is more preferable.

The deletion, mutation or repression of expression of the acyl-ACP thioesterase gene of the present invention from a host genome can be conducted by a method of partially or wholly removing a target gene from a genome, replacing the target gene by other genes, inserting other DNA fragments into the target gene, or providing mutation in an active site, a substrate-binding site, or a transcription or translation initiation region of the target gene.

The above method of deletion, mutation or repression of expression can employ, for example, homologous recombination techniques. Specifically, a linear DNA fragment containing upstream and downstream regions of a target gene but containing no target gene is constructed by a method such as PCR, and the resultant DNA fragment is incorporated into a host cell to cause double crossover homologous recombination on the side upstream and downstream of the target gene of the host genome, and then the target gene on the genome can be deleted or substituted for other gene fragment. Moreover, a target gene into which mutation such as nucleotide substitution and nucleotide insertion is introduced is constructed by a method such as PCR, and the resulting gene is incorporated into a host cell to cause double crossover homologous recombination in two regions outside the mutation site in the target gene of the host genome, and then a function of the target gene on the genome can be deteriorated or lost. Moreover, a cyclic recombinant plasmid is prepared by introducing a DNA fragment partially containing a target gene into a suitable plasmid vector, and the resultant plasmid is incorporated into a host cell to cause homologous recombination in part, of region of the target gene on the host genome and to split the target gene of the host genome, and then a function of the target gene can be deteriorated or lost.

The method of deletion, mutation or repression of expression of a target gene using homologous recombination can be conducted with, for example, reference to literature such as Besher et al., Methods in molecular biology, 1995, vol. 47, p. 291-302. In particular, when the host is the algae belonging to the genus *Nannochloropsis*, specific gene in a genome can be deleted or broken, with referring to literature such as Oliver Kilian, et al., Proceedings of the National Academy of Sciences of the United States of America, 2011, vol. 108(52), by homologous recombination method.

The selection of transformants with deletion or the like of the target gene can be made by a method of extracting genome DNA from the transformant and performing PCR to amplify a region containing the target gene site, a southern blotting method using a DNA probe to be bonded with the target gene region, or the like.

With regard to the transformant of the second embodiment, the acyl-ACP thioesterase gene of the present invention does not function. Therefore, the fatty acid composition of the lipid produced is considered to change from the composition original to the host. More specifically, the transformant can produce a lipid in which the fatty acid composition in the lipids is modified.

4. Method of Producing Lipid

In the transformant of the first embodiment according to the present invention, productivity of the medium chain fatty acids or the lipids containing these fatty acids as the components is improved in comparison with the host. Accordingly, if the transformant of the present invention is cultured, under suitable conditions and then the medium chain fatty acids or the lipids containing these fatty acids as the components are collected from a cultured product obtained, the medium chain fatty acids or the lipids containing these fatty acids as the components can be efficiently produced.

From a viewpoint of improvement in the productivity of lipids, the method of producing a lipid of the present invention preferably includes a step of obtaining a cultured product, by culturing, under suitable conditions, the transformant having the introduced gene encoding the acyl-ACP thioesterase; and a step of collecting the lipid from the resulting cultured product.

In addition, an expression "culture the transformant" in the present specification means culturing or growing of the microorganisms, the algae, the plants or the animals, or cells or tissues thereof, including cultivating of the plants in soil or the like. Herein, the "cultured product" includes a transformant itself subjected to cultivation or the like, in addition to the medium used for culture.

The culture condition can be suitably selected in accordance with the host of the transformant, and any ordinary used culture condition can fee employed.

Further, from a viewpoint of the production efficiency of lipids, substrates of acyl-ACP thioesterase or precursor substances participating in the fatty acid biosynthesis system, such as glycerol, acetic add or malonic acid, may be added to the medium.

For example, in the case of using *Escherichia coli* as the host for transformation, culture may be carried out in LB medium or Overnight Express Instant TB Medium (manufactured by Novagen) at 30° C. to 37° C. for half a day to 1 day.

In the case of using *Arabidopsis thaliana* as the host for transformation, growth may be carried out at soil under the temperature conditions of 20° C. to 25° C., by continuously irradiating white light or under light illumination conditions of a light period of 16 hours and a dark period of 8 hours, for one to two months.

When the host of the transformant is the algae, medium based on natural seawater or artificial seawater may be used. Alternatively, commercially available culture medium may also be used. Specific examples of the culture medium include f/2 medium, ESM medium, Daigo IMK medium, L1 medium and MNK medium. Above all, from viewpoints of an improvement in the productivity of lipids and a nutritional ingredient concentration, f/2 medium, ESM medium or Daigo IMK medium is preferred; f/2 medium or Daigo IMK medium is more preferred; and f/2 medium is further preferred. For growth promotion of the algae and an improvement in productivity of fatty acids, a nitrogen source, a phosphorus source, metal salts, vitamins, trace metals or me like can be appropriately added to the culture medium. An amount of the algae to be seeded to the culture medium is not particularly limited, in view of viability, the amount is preferably 1% to 50% (vol/vol), and more preferably 1% to 10% (vol/vol), per culture medium. Culture temperature is not particularly limited within the range in which the temperature does not adversely affect growth of the algae, and is ordinarily in the range of 5° C. to 40° C. From viewpoints of the growth promotion of the algae, the improvement in productivity of fatty acids, and reduction of production cost, the temperature is preferably 10° C. to 35° C., and more preferably 15° C. to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably in the range of 100 lx to 50,000 lx, more preferably in the range of 300 lx to 10,000 lx, and further preferably in the range of 1,000 lx to 8,000 lx. Moreover, an interval of the light irradiation is not particularly limited. From the viewpoints in a manner similar to the viewpoints described above, the irradiation is preferably performed under a light and dark cycle, in 24 hours, a light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion or the improvement in the productivity of fatty acids, the concentration is preferably from 0.03% (which is the same degree as the concentration under atmospheric conditions) to 10%, more preferably from 0.05% to 5%, further preferably from 0.1% to 3%, and furthermore preferably from 0.3% to 1%. A concentration of the carbonate is not particularly limited.

When the sodium hydrogen carbonate is used, for example, from viewpoints of the growth promotion and the improvement in the productivity of fatty acids, the concentration is preferably from 0.01% to 5% by mass, more preferably from 0.05% to 2% by mass, and further preferably from 0.1% to 1% by mass.

A culture time is not particularly limited, and the culture may be performed for a long time (for example, about 150 days) so that an alga body in which the lipid is accumulated at a high concentration can grow at a high concentration. From viewpoints of the growth promotion of the algae, the improvement in the productivity of fatty acids, and the reduction of production cost, the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture is preferred.

Lipids produced in the transformant is collected by an ordinary method used for isolating lipid components and the like contained in the living body of the transformant. For example, lipid components can be isolated and collected from the above-described cultured product or the transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the cultured product or the transformant through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

In the acyl-ACP thioesterase of the present invention, specificity to the medium chain acyl-ACP, further, C12 to C16 acyl-ACP, particularly C12 acyl-ACP or C14 acyl-ACP is high, in the transformant of the first embodiment of the present invention, the ratio of the content of fatty acids having 8 to 16 carbon atoms, preferably the ratio of the content of fatty acids having 12 to 16 carbon atoms, more preferably fatty acids having 12 to 14 carbon atoms, further preferably fatty acids having 12 or 14 carbon atoms, and furthermore preferably fatty acids having 14 carbon atoms each in the total fatty acid components increases. Therefore, the production method in which the transformant is used of the present invention can be preferably applied to production of lipids, particularly medium chain fatty acids, preferably fatty acids having 8 to 16 carbon atoms, more preferably fatty acids having 12 to 16 carbon atoms, further preferably fatty acids having 12 to 14 carbon atoms, furthermore preferably ratty acids having 12 or 14 carbon atoms, and furthermore preferably fatty acids having 14 carbon atoms or a lipids containing these fatty acids as components.

The lipids produced in the production method of the present invention preferably contain fatty acids or fatty acid compounds, and more preferably contain fatty acids or fatty acid ester compounds thereof, in view of usability thereof. Specifically, the lipids produced in the production method of the present invention preferably contain fatty acids having 8 or more and 18 or less carbon atoms or fatty acid ester compounds thereof, more preferably contain fatty acids having 12 or more and 16 or less carbon atoms or fatty acid ester compounds thereof, further preferably contain fatty acids having 12 or more and 14 or less carbon atoms or fatty acid ester compounds thereof, furthermore preferably contain fatty acids having 12 or 14 carbon atoms or fatty acid ester compounds thereof, and furthermore preferably contain fatty acids having 14 carbon atoms or fatty add ester compounds thereof. From usability for a surfactant or the like, the fatty acid or the fatty acid ester compound thereof contained in the lipid is preferably a fatty acid having 8 to 16 carbon atoms or a fatty acid ester thereof, more preferably a fatty acid having 12 to 16 carbon atoms or a fatty acid ester thereof, further preferably a fatty acid having 12 to 14 carbon atoms or a fatty acid ester compound thereof, furthermore preferably a fatty acid having 12 or 14 carbon atoms or a fatty acid ester compound thereof, and furthermore preferably a fatty acid having 14 carbon atoms or a fatty acid ester compound thereof.

From a viewpoint of the productivity, the fatty acid ester compound is preferably a simple lipid or a complex lipid, more preferably a simple lipid, and further preferably a triacylglycerol.

The fatty acids and lipids obtained by the production method or the transformant of the present invention can be utilized for food, as well as an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods, transformants, proteins, and genes described below.

<1> A method of producing a lipid, containing the steps of:
culturing a transformant in which a gene encoding any one of the following proteins (A) to (C) is introduced into a host, and
collecting a lipid from the cultured product:
(A) a protein consisting of the amino acid sequence of the 91st to 348th positions set forth in SEQ ID NO: 1;
(B) a protein consisting of an amino acid sequence having 80% or more identity with the amino acid sequence of the 91st to 348th positions set forth in SEQ ID NO: 1 and having acyl-ACP thioesterase activity; and
(C) a protein containing the amino acid sequence of the protein (A) or (B), and having acyl-ACP thioesterase activity.

<2> A method of enhancing productivity of fatty acids or a lipid containing the fatty acids as components produced in a cell of a transformant, containing the step of introducing a gene encoding any one of the proteins (A) to (C) into a host.

<3> The method described in the above item <2>, wherein the lipid is a medium chain fatty acid or a lipid containing the medium chain fatty acids as the components.

<4> A method of modifying the composition of a lipid, containing the steps of:
introducing a gene encoding any one of the proteins (A) to (C) into a host, and thereby obtaining a transformant, and
enhancing productivity of medium chain fatty acids or a lipid containing the medium chain fatty acids as components produced in a cell of the transformant, to modify the composition of fatty acids or a lipid in all fatty acids or all lipids to be produced.

<5> A method of producing a lipid, containing the steps of:
culturing a transformant in which the expression of a gene encoding any one of the proteins (A) to (C) is enhanced, and
collecting a lipid from the cultured product:

<6> A method of enhancing productivity of fatty acids or a lipid containing the fatty acids as components produced in a cell of a transformant, containing the step of enhancing the expression of a gene encoding any one of the proteins (A) to (C).

<7> The method described in the above item <6>, wherein the lipid is medium chain fatty acids or a lipid containing the medium chain fatty acids as the components.

<8> A method of modifying the composition of a lipid, containing the step of:
enhancing the expression of a gene encoding any one of the proteins (A) to (C), and
enhancing productivity of medium chain fatty acids or a lipid containing the medium chain fatty acids as components produced in a cell of a transformant, to modify the composition of fatty acids or a lipid in all fatty acids or all lipids to be produced.

<9> The method described in any one of the above items <5> to <9>, containing the step of introducing a gene encoding any one of the proteins (A) to (C) into a host, and enhancing the expression of the gene.

<10> The method described in any one of the above items <1> to <9>, wherein the identity of the protein (B) with the amino acid sequence of the 91st to 348th positions set forth in SEQ ID NO: 1 is 85% or more, preferably 90% or more, more preferably 95% or more, further preferably 98% or more, furthermore preferably 97% or more, furthermore preferably 98% or more, and furthermore preferably 99% or more.

<11> The method described in any one of the above items <1> to <10>, wherein the protein (B) consists of an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 8 or less amino acids, furthermore preferably 1 or more and 5 or less amino acids, furthermore preferably 1 or more and 4 or less amino acids, furthermore preferably 1 or more and 3 or less amino acids, and furthermore preferably 1 or 2 amino acids, are deleted, substituted, inserted or added to the amino acid sequence of the 91st to 348th positions set forth in SEQ ID NO: 1; and has acyl-ACP thioesterase activity.

<12> The method described in any one of the above items <1> to <9>, wherein the protein (C) consists of an amino acid sequence in which an amino acid on an N-terminal side is deleted at an arbitrary position of the 1st to 90th positions set forth in SEQ ID NO: 1.

<13> The method described in any one of the above items <1> to <9>, wherein the protein (C) is any one of the following proteins (C1) to (C7);
(C1) a protein consisting of the amino acid sequence of the 1st to 348th positions set forth in SEQ ID NO: 1;
(C2) a protein consisting of the amino acid sequence of the 61st to 348th positions set forth in SEQ ID NO: 1;
(C3) a protein consisting of the amino acid sequence of the 71st to 348th positions set forth in SEQ ID NO: 1;
(C4) a protein consisting of the amino acid sequence of the 74th to 348th positions set forth in SEQ ID NO: 1;
(C5) a protein consisting of the amino acid sequence of the 81st to 348th positions set forth in SEQ ID NO: 1;
(C6) a protein consisting of an amino acid sequence having 80% or more identity, preferably 85% or more identity, more preferably 90% or more identity, further preferably 95% or more identity, furthermore preferably 96% or more identity, furthermore preferably 97% or more identity, furthermore preferably 98% or more identity, and furthermore preferably 99% or more identity, with the amino acid sequence of any one of the proteins (C1) to (C5), and having acyl-ACP thioesterase activity; and
(C7) a protein consisting of an amino acid sequence in which 1 or several amino acids, preferably 1 or more and 20 or less amino acids, more preferably 1 or more and 15 or less amino acids, further preferably 1 or more and 10 or less amino acids, furthermore preferably 1 or more and 8 or less amino acids, furthermore preferably 1 or more and 5 or less amino acids, furthermore preferably 1 or more and 4 or less amino acids, furthermore preferably 1 or more and 3 or less amine acids, and furthermore preferably 1 or 2 amino acids, are deleted, substituted, inserted or added to the amino acid sequence of any one of the proteins (C1) to (C5), and having acyl-ACP thioesterase activity.

<14> The method described in any one of the above items <1> to <13>, wherein the gene encoding any one of the proteins (A) to (C) is a gene consisting of any one of the following DNAs (a) to (c);
(a) a DNA consisting of the nucleotide sequence of the 271st to 1,047th positions set forth in SEQ ID NO: 2;
(b) a DNA consisting of a nucleotide sequence having 80% or more identity, preferably 85% or more identity, more preferably 90% or more identity, further preferably 95% or more identity, furthermore preferably 96% or more identity, furthermore preferably 97% or more identity, furthermore preferably 98% or more identity, and furthermore preferably 99% or more identity, with the nucleotide sequence of the 271st to 1,047th positions set forth in SEQ ID NO: 2, and encoding a protein having acyl-ACP thioesterase activity; and
(c) a DNA containing the nucleotide sequence of the DNA (a) or (b), and encoding a protein having acyl-ACP thioesterase activity.

<15> The method described the above item <14>, wherein the DNA (b) is a DNA consisting of a nucleotide sequence in which 1 or several nucleotides, preferably 1 or more and 20 or less nucleotides, more preferably 1 or more and 15 or less nucleotides, further preferably 1 or more and 10 or less nucleotides, furthermore preferably 1 or more and 8 or less nucleotides, furthermore preferably 1 or more and 5 or less nucleotides, furthermore preferably 1 or more and 4 or less nucleotides, furthermore preferably 1 or more and 3 or less nucleotides, and furthermore preferably 1 or 2 nucleotides, are deleted, substituted, inserted or added to the nucleotide sequence of the DNA (a), and encoding a protein having acyl-ACP thioesterase activity, or a DNA capable of hybridizing with a DNA consisting of a nucleotide sequence complementary with the DNA (a) under a stringent condition, and encoding a protein having acyl-ACP thioesterase activity.

<16> The method described the above item <14>, wherein the DNA (c) consists of a nucleotide sequence in which nucleotides on a 5'-terminal side are deleted at an arbitrary position of the 1st to 270th positions set forth in SEQ ID NO: 2.

<17> The method described in the above item <14> wherein the DNA (c) is any one of the following DNAs (c1) to (c7):
(c1) a DNA consisting of the nucleotide sequence of the 1 st to 1,047th positions set forth in SEQ ID NO: 2;
(c2) a DNA consisting of the nucleotide sequence of the 181st to 1,047th positions set forth in SEQ ID NO: 2;
(c3) a DNA consisting of the nucleotide sequence of the 211th to 1,047th positions set forth in SEQ ID NO: 2;
(c4) a DNA consisting of the nucleotide sequence of the 220th to 1,047th positions set forth in SEQ ID NO: 2;

(c5) a DNA consisting of the nucleotide sequence of the 241st to 1,047th positions set forth in SEQ ID NO: 2;
(c6) a DNA consisting of a nucleotide sequence having 80% or more identity, preferably 85% or more identity, more preferably 90% or more identity, further preferably 95% or more identity, furthermore preferably 98% or more identity, furthermore preferably 97% or more identity, furthermore preferably 98% or more identity, and furthermore preferably 99% or more identity, with the nucleotide sequence of any one of the DNAs (c1) to (c5), and encoding a protein having acyl-ACP thioesterase activity; and
(c7) a DNA consisting of a nucleotide sequence in which 1 or several nucleotides, preferably 1 or more and 20 or less nucleotides, more preferably 1 or more and 15 or less nucleotides, further preferably 1 or more and 10 or less nucleotides, furthermore preferably 1 or more and 8 or less nucleotides, furthermore preferably 1 or more and 5 or less nucleotides, furthermore preferably 1 or more and 4 or less nucleotides, furthermore preferably 1 or more and 3 or less nucleotides, and furthermore preferably 1 or 2 nucleotides, are deleted, substituted, inserted or added to the nucleotide sequence of any one of the DNAs (c1) to (c5), and encoding a protein having acyl-ACP thioesterase activity.
<18> The method described in any one of the above items <1> to <17>, wherein a host, of the transformant is a microorganism.
<19> The method described in the above item <18>, wherein the microorganism is *Escherichia coil*.
<20> The method described in the above item <18>, wherein the microorganism is a microalga.
<21> The method described in the above item <20>, wherein the microalga is an alga belonging to the genus *Nannochloropsis*, preferably *Nannochloropsis oculata*.
<22> The method described in any one of the above items <1> to <21>, wherein the lipid contains a medium chain fatty acid or a fatty acid ester compound thereof, preferably a fatty acid having 8 or more and 16 or less carbon atoms or a fatty acid ester compound thereof, more preferably a fatty acid having 12 or more and 16 or less carbon atoms or a fatty acid ester compound thereof, further preferably a fatty acid having 12 or more and 14 or less carbon atoms or a fatty acid ester compound thereof, furthermore preferably a fatty acid having 12 or 14 carbon atoms or a fatty acid ester compound thereof, and furthermore preferably a fatty add having 14 carbon atoms or a fatty acid ester compound thereof.
<23> The proteins (A) to (C) specified in any one of the above items <1> to <22>.
<24> A gene encoding the protein described in the above item <23>.
<25> A gene consisting of any one of the DNAs (a) to (c) specified in any one of the above items <1> to <22>.
<26> A recombinant vector, containing the gene described in the above item <24> or <25>.
<27> A transformant, which is obtained by introducing the gene described in the above item <24> or <25> or the recombinant vector described in the above item <26> into a host.
<28> A method of producing a transformant containing introducing the gene described in the above item <24> or <25> or the recombinant vector described in the above item <26> into a host.
<29> A transformant, wherein the expression of the gene described in the above item <24> or <25> is promoted.
<30> The transformant or the method of producing the same described in any one of the above items <27> to <29>, wherein the host of the transformant is a microorganism.
<31> The transformant or the method of producing the same described in the above item <30>, wherein the microorganism is *Escherichia coli*.
<32> The transformant or the method of producing the same described in the above item <30>, wherein the microorganism is a microalga.
<33> The transformant or the method of producing the same described in the above item <32>, wherein the microalga is an alga belonging to the genus *Nannochloropsis*, preferably *Nannochloropsis oculata*.
<34> Use of the protein, the gene, the recombinant vector, the transformant or a transformant obtained by the method of producing a transformant described in any of the above items <23> to <33>, for producing a lipid.
<35> The use described in the above item <34>, wherein the lipid contains a medium chain fatty add or a fatty add ester compound thereof, preferably a fatty acid having 8 or more and 16 or less carbon atoms or a fatty acid ester thereof, more preferably a fatty acid having 12 or more and 16 or less carbon atoms or a fatty acid ester compound thereof, further preferably a fatty acid having 12 or more and 14 or less carbon atoms or a fatty acid ester compound thereof, furthermore preferably a fatty acid having 12 or 14 carbon atoms or a fatty acid ester compound thereof, and furthermore preferably a fatty acid having 14 carbon atoms or a fatty acid ester compound thereof.
<36> A method of modifying a fatty acid composition in a lipid, containing a step of deletion, mutation or repression of expression of the gene from a host having the gene described in the above item <24> or <25>.

EXAMPLES

Hereinafter, the present invention will be described more in detail with reference to Examples, but the present invention is not limited thereto. Herein, the nucleotide sequences of the primers used in Examples are shown in Tables 1 and 2.

TABLE 1

| Primer No. | Nucleotide sequence (5'→3') | SEQ ID NO: |
|---|---|---|
| 3 | gcggccgctctagagatgagaatacct tcccttatc | SEQ ID NO: 3 |
| 4 | acaaaatattaacgcctacgtcgtgcc catgttcat | SEQ ID NO: 4 |
| 5 | ctctagagcggccgccaccg | SEQ ID NO: 5 |
| 6 | gcgttaatattttgttaaaattcg | SEQ ID NO: 6 |
| 7 | gcggccgctctagagagcagaccaaga tgcagccc | SEQ ID NO: 7 |
| 8 | gcggccgctctagaggtcacgactgcc gctactgc | SEQ ID NO: 8 |
| 9 | gcggccgctctagaggccgctactgct tcatctgc | SEQ ID NO: 9 |
| 10 | gcggccgctctagagacagaggaagcg gaaaaccc | SEQ ID NO: 10 |
| 11 | gcggccgctctagagcaaggagtattc atcgagca | SEQ ID NO: 11 |
| 12 | gcggccgctctagagtacgggatggtc taccactc | SEQ ID NO: 12 |

TABLE 2

| Primer No. | Nucleotide sequence (5'→3') | SEQ ID NO: |
|---|---|---|
| 15 | cttttttgtgaagcaatggccaagttgaccagtgccg | SEQ ID NO: 15 |
| 16 | tttcccccatcccgattagtcctgctcctcggccac | SEQ ID NO: 16 |
| 17 | cgagctcggtacccgactgcgcatggattgaccga | SEQ ID NO: 17 |
| 18 | tgcttcacaaaaaagacagcttcttgat | SEQ IL NO: 18 |
| 19 | tcgggatggggaaaaaaacctctg | SEQ ID NO: 19 |
| 20 | actctagaggatcccctttcgtaaataaatcagctc | SEQ ID NO: 20 |
| 22 | gggatcctctagagtcgacc | SEQ ID NO: 22 |
| 23 | cgggtaccgagctcgaattc | SEQ ID NO: 23 |
| 24 | cagcccgcatcaacaatgagaataccttcccttatcc | SEQ ID NO: 24 |
| 25 | ctcttccacagaagcctacgtcgtgcccatgttca | SEQ ID NO: 25 |
| 26 | cgagctcggtacccgttcttccgcttgttgctgcc | SEQ ID NO: 26 |
| 27 | tgttgatgcgggctgagattggtgg | SEQ ID NO: 27 |
| 28 | gcttctgtggaagagccagtg | SEQ ID NO: 28 |
| 29 | ggcaagaaaagctgggggaaaagacagg | SEQ ID NO: 29 |
| 32 | ccagcttttcttgccactgcgcatggattgaccga | SEQ ID NO: 32 |
| 33 | cgcggtgttgcgcgcgccgctactgcttcatctgc | SEQ ID NO: 33 |
| 34 | cagcccgcatcaacaatgaagaccgccgctctcctc | SEQ ID NO: 34 |
| 35 | gcgcgcaacaccgcgggtgcgggagaac | SEQ ID NO: 35 |

Examples 1 Preparation of Acyl-ACP Thioesterase Gene, Transformation of *Escherichia Coli*, and Producing Lipid by Transformant (1) Preparation of Acyl-ACP Thioesterase Gene Derived from *Nannochloropsis Oculata*

Total RNA of *Nannochloropsis oculata* strain NIES2145 (obtained from National Institute for Environmental Studies (NIES)) was extracted. The cDNA was obtained by reverse transcription using the total RNA, and SuperScript™ III First-Strand Synthesis SuperMix for qRT-PCR (manufactured by invitrogen). PCR using a pair of the primer Nos. 3 and 4 shown in Table 1 and the above cDNA as a template, was carried out to prepare a gene fragment consisting of the nucleotide sequence set forth in SEQ ID NO: 2. Hereinafter, this gene is referred to as "NoTE2 gene", and a protein encoded by the gene is referred to as "NoTE2" (SEQ ID NO: 1).

Moreover, using a plasmid vector pBluescriptII SK(−) (manufactured by Stratagene) as a template, and a pair of the primer Nos. 5 and 6 shown in Table 1, the pBluescriptII SK(−) was amplified by PCR. Then, the resultant template was subjected to digestion by restriction enzyme DpnI (manufactured by TOYOBO) treatment.

A plasmid in which a whole length of a NoTE2 gene was cloned was prepared by purifying these two fragments using High Pure PCR Product Purification Kit (manufactured by Roche Applied Science Corporation), and then fusing the resultant material by using In-Fusion HD Cloning Kit (manufactured by Clontech, Inc.) to perform transformation into *Escherichia coli* DH5α strain Competent Cells (manufactured by Takara Bio), plasmid extraction, and confirmation of a nucleotide sequence of a cloning fragment according to an ordinary method.

(2) Construction of Plasmid for NoTE2 Gene Expression

In the amino acid sequence of NoTE2 set forth in SEQ ID NO: 1, a sequence in the vicinity of N-terminal 1st to 73rd positions was presumed to be a chloroplast transit signal sequence. Then, a plurality of plasmids for NoTE2 gene expression, in which an N-terminal region containing the presumed chloroplast transit signal sequence was deleted at various lengths, were constructed.

PCR was carried out by using the plasmid as a template, and a pair of any one of the primer Nos. 7 to 12 and the primer No. 5 shown in Table 1, and obtained gene fragments were purified and fused in a manner similar to the method described above, to construct a plasmid for NoTE2 gene expression NoTE2_61, NoTE2_71, NoTE2_74, NoTE2_81, NoTE2_91, and NoTE2_101, respectively.

Herein, the plasmid NoTE2_61 was constructed in the form of removing the 1st to 60th positions on an N-terminal side of an amino acid sequence set forth in SEQ ID NO: 1, and had a nucleotide sequence of the 181st to 1,047th positions set forth in SEQ ID NO: 2 corresponding to the amino acid sequence of the 61st to 348th positions set forth in SEQ ID NO: 1 and the termination codon as a NoTE2 gene. In a similar manner, the plasmid NoTE2_71, the plasmid NoTE2_74, the plasmid NoTE2_81, the plasmid NoTE2_91, and the plasmid NoTE2_101, were constructed in the form of removing the 1st to 70th positions, the 1st to 73rd positions, the 1st to 80th positions, the 1st to 90th positions, and the 1st to 100th positions, on an N-terminal side of an amino acid sequence set forth in SEQ ID NO: 1, respectively. Further, these plasmids were constructed in the form of expressing an amino acid sequence of the 1st to 29th positions on an N-terminal side of a LacZ protein derived from the plasmid vector pBluescriptII SK(−), to the upstream of the removed sites on an N-terminal side of the amino acid sequence set forth in SEQ ID NO: 1.

(3) Introduction of Plasmid for NoTE2 Gene Expression into *Escherichia Coli*

An *Escherichia coli* mutant strain, strain K27 (fadD88) (Overath et al, Eur. J. Biochem., vol. 7, 559-574, 1969), was transformed by a competent cell transformation method, using the various plasmids for NoTE2 gene expression. The transformed *Escherichia coli* strain K27 was inoculated in LB agar medium containing 50 µg/mL of Ampicillin sodium (Bacto Trypton 1%, Yeast Extract 0.5%, NaCl 1%, and Agar 1.5%), and was stand overnight at 30° C. The colony thus obtained was inoculated to 2 mL of Overnight Express instant TB medium (Novagen) (containing 50 µg/mL of Ampicillin sodium) and was subjected to shaking culture (160 rpm) at 30° C. After 24 hours cultivation, lipid components contained in the culture fluid were analyzed by the method described below. In addition, as a negative control, the *Escherichia coli* strain K27 transformed with the plasmid vector pBluescriptII SK(−) was also subjected to the same experiment.

(4) Extraction of Lipid From Culture Fluid and Analysis of Fatty Acids Contained Therein To 1 mL of the culture fluid, 50 µL of 1 mg/mL 7-pentadecanone (methanol solution) as an internal standard was added, and then 0.5 mL of chloroform and 1 mL of methanol were further added thereto. The mixture was vigorously stirred and then was left for 10 minutes or more. Further, 0.5 mL of chloroform and 0.5 mL of 1.5% KCl were added thereto. The mixture was stirred and centrifuged for 5 minutes at 3,000 rpm, and then the chloroform layer (lower layer) was collected with pasteur pipette.

A nitrogen gas was blown onto the resultant chloroform layer to be dried into solid, 0.7 mL of 0.5 N potassium hydroxide/methanol solution was added thereto, and the resultant mixture was kept warm at 30° C. for 30 minutes.

amounts of each of the fatty acids thus obtained, and ratio of amounts of each of the fatty acids in the total amount of the fatty acids was calculated.

The results are shown in Table 3. Herein, in Table below, "TFA" presents a total amount of fatty acids, and "Fatty Acid Composition (% TFA)" presents a ratio of amount of each fatty acid (weight percent) relative to a weight of the total fatty acid. Moreover, description of "Cx:y" represents a fatty acid having "x" as the number of carbon atoms, and "y" as the number of double bonds, and the expressions "C17:0Δ" and "C19:0Δ" designate cis-9,10-Methylen-hexadecanoic acid and cis-11,12-Methylen-octadecanoic acid, respectively.

TABLE 3

| Introduced plasmid | TFA (mg/L) | Fatty acid composition (% TFA) | | | | | | | |
|---|---|---|---|---|---|---|---|---|---|
| | | C12:0 | C14:1 | C14:0 | C16:1 | C16:0 | C17:0Δ | C18:1 | C19:0Δ |
| pBS | 182.3 | 0.7 | 0.0 | 4.8 | 1.7 | 48.1 | 28.7 | 4.0 | 11.9 |
| NoTE2_61 | 192.1 | 1.0 | 2.8 | 9.6 | 3.2 | 43.9 | 23.8 | 6.3 | 9.4 |
| NoTE2_71 | 236.0 | 1.4 | 5.7 | 12.7 | 4.9 | 40.8 | 19.4 | 8.1 | 7.0 |
| NoTE2_74 | 203.2 | 1.2 | 5.7 | 11.6 | 5.0 | 40.6 | 19.9 | 8.6 | 7.4 |
| NoTE2_81 | 231.9 | 1.6 | 7.0 | 13.4 | 4.8 | 38.7 | 18.3 | 8.5 | 7.6 |
| NoTE2_91 | 208.7 | 1.2 | 6.2 | 11.4 | 5.8 | 40.7 | 18.5 | 10.0 | 6.2 |
| NoTE2_101 | 163.3 | 0.7 | 0.5 | 5.5 | 2.0 | 47.6 | 27.4 | 6.0 | 10.4 |

Then, 1 mL of 14% methanol solution of boron trifluoride (manufactured by Sigma-Aldrich) was added to the sample, and the mixture was kept warm at 80° C. for 10 minutes. Thereafter, 0.5 mL of hexane and 0.5 mL of saturated saline were added thereto, and the mixture was vigorously stirred and then was left for 10 minutes or more at room temperature. Then, the hexane layer (upper layer) was collected to obtain fatty acid methyl esters.

Under the measuring conditions as follows, the obtained fatty acid methyl esters were provided for gas chromatographic analysis.
<Gas Chromatography Conditions>
Capillary column: DB-1 MS (30 m×200 µm×0.25 µm, manufactured by J&W Scientific)
Mobile phase: high purity helium
Flow rate inside the column: 1.0 mL/min
Temperature rise program: 100° C. (for 1 min.)→10° C./min→300° C. (for 5 min.)
Equilibration time: for 1 min.
Injection port: split injection (split ratio: 100:1)
Pressure: 14.49 psi, 104 mL/min
Amount of injection: 1 µL
Cleaning vial: methanol/chloroform
Detector temperature: 300° C.

Further, the fatty acid methyl esters were identified by providing the identical sample for a gas chromatography-mass spectrometry analysis under identical conditions described above.

Amounts of the fatty acid methyl esters were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of the fatty acids was calculated by summing the As shown in Table 3, in the strain having the introduced plasmids for NoTE2 gene expression NoTE2_61, NoTE2_71, NoTE2_74, NoTE2_81 and NoTE2_91, a ratio of each of the C12:0, C14:1, C14:0, and C16:1 fatty acids in the total fatty acid significantly increased in comparison with the strain having the introduced the negative control plasmid vector pBluescriptII SK(−) ("pBS" in Table). In particular, a ratio of C14 fatty acids (C14:1 and C14:0 fatty acids) extremely increased. Further, in the strain having the introduced these plasmids for NoTE2 gene expression, the total amount of fatty acids (TFA) also increased. From these results, it was confirmed that the proteins encoding the gene introduced into the plasmid NoTE2_81, NoTE2_71, NoTE2_74, NoTE2_81, and NoTE2_91 had acyl-ACP thioesterase activity. Moreover, these proteins extremely increased a ratio and productivity of the C12 and C14 fatty acids. Therefore, it was considered that these proteins are acyl-ACP thioesterases having high specificity to the C12 and C14 ratty acids, particularly C14 fatty acids.

On the other hand, in the strain having the introduced plasmids NoTE2_101, the fatty acid composition hardly changed and the total amount of fatty acids also did not increased in comparison with the negative control. Therefore, it was considered that the protein encoding the gene introduced into the plasmid NoTE2_101 hardly had acyl-ACP thioesterase activity.

From the results described above, it is recognized that the protein having the region of at least 91st to 348th positions in the amino acid sequence set forth in SEQ ID NO: 1 designates acyl-ACP thioesterase activity.

Examples 2 Transformation of *Nannochloropsis Oculata* by Acyl-ACP Thioesterase Gene Derived From *Nannochloropsis Oculata*, and Producing Lipid by Transformant (1) Construction of Plasmid for Zeocin Resistance Gene Expression A zeocin resistance gene (SEQ ID NO: 13), and a tubulin promoter sequence (SEQ ID NO: 14) derived from *Nanno-*

*chloropsis gaditana* strain CCMP 526 described in a literature (Randor Radakovits, et al., Nature Communications, DOI: 10.1038/ncomms1688, 2012) were artificially synthesized. Using the thus-synthesized DNA fragments as a template, and a pair of the primer Nos. 15 and 16, and a pair of the primer Nos. 17 and 18 shown in Table 2, PCR was carried out, to amplify the zeocin resistance gene and the tubulin promoter sequence, respectively.

Further, using a genome of *Nannochloropsis oculata* strain NIES2145 as a template, and a pair of the primer Nos. 19 and 20 shown in Table 2, PCR was carried out to amplify the heat shock protein terminator sequence (SEQ ID NO: 21).

Furthermore, using a plasmid vector pUC19 (manufactured by Takara Bio) as a template, and a pair of the primer Nos. 22 and 23 shown in Table 2, PCR was carried out to amplify the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression.

Herein, the plasmid consisted of the pUC19 vector sequence and an insert sequence in which the tubulin promoter sequence, the zeocin resistance gene and the heat shock protein terminator sequence were linked in this order.

(2) Construction of Plasmid for NoTE2 Gene Expression

Using the cDNA derived from *Nannochloropsis oculata* strain NIES2145 prepared in Example 1 as a template, and a pair of the primer Nos. 24 and 25 shown in Table 2, PCR was carried out to prepare gene fragments consisting of the nucleotide sequence set forth in SEQ ID NO: 2.

Further, using a genome of *Nannochloropsis oculata* strain NIES2145 as a template, and a pair of the primer Nos. 26 and 27, and a pair of the primer Nos. 28 and 29 shown in Table 2, PCR was carried out to prepare the LDSP promoter sequence (SEQ ID NO: 30) and the VCP1 terminator sequence (SEQ ID NO: 31).

Furthermore, using the above-described plasmid for zeocin resistance gene expression as a template, and a pair of the primer Nos. 32 and 23 shown in Table 2, PCR was carried out to amplify a fragment containing the cassette for zeocin resistance gene expression (the tubulin promoter sequence, the zeocin resistance gene, and the heat shock protein terminator sequence) and the pUC19 sequence.

These four amplified fragments were fused by a method in a manner similar to described above, to construct plasmids for NoTE2 gene expression (NoTE2-Nanno).

Herein, the plasmid consisted of the pUC19 vector sequence and an insert sequence in which the LDSP promoter sequence, the NoTE2 gene, the VCP1 terminator sequence, the tubulin promoter sequence, the zeocin resistance gene and the heat shock protein terminator sequence were linked in this order.

Furthermore, using the plasmid for NoTE2 gene expression (NoTE2-Nanno) as a template, and a pair of the primer Nos. 33 and 27 shown in Table 2, PCR was carried out to prepare gene fragments.

Moreover, using the cDNA of *Nannochloropsis oculata* strain NIES2145 as a template, and a pair of the primer Nos. 34 and 38 as shown in Table 2, PCR was carried out to prepare the VCP1 chloroplast transit signal (SEQ ID NO: 36).

These fragments were fused by a method in a manner similar to described above, to construct plasmids for NoTE2 gene of *Nannochloropsis* expression (NoTE2_74-Nanno).

Herein, the plasmid consisted of the pUC19 vector sequence and an insert sequence in which the LDSP promoter sequence, the NoTE2 gene in which the VCP1 chloroplast transit signal was linked to the 5'-terminal side of the nucleotide sequence encoding an amino add sequence of the 74th to 348th positions set forth in SEQ ID NO: 1 (hereinafter, also referred to as "NoTE2_74 gene"), the VCP1 terminator sequence, the tubulin promoter sequence, the zeocin resistance gene and the heat shock protein terminator sequence were linked in this order.

(3) Introduction of Cassette for NoTE2 Gene Expression into *Nannochloropsis Oculata*

Using the above-described plasmids for NoTE2 gene expression (NoTE2-Nanno and NoTE2_74-Nanno) as a template, respectively, and a pair of the primer Nos. 20 and 28 shown in Table 2, PCR was carried out to amplify a cassette for NoTE2 gene expression (a DNA fragment containing the LDSP promoter sequence, the NoTE2 gene or the NoTE2_74 gene, the VCP1 terminator sequence, the tubulin promoter sequence, the zeocin resistance gene, and the heat shock protein terminator sequence).

The amplified DNA fragments were purified using High Pure PCR Product Purification Kit (manufactured by Roche Applied Science). Herein, sterilized water was used for elution upon purification without using an elution buffer included in the kit.

About $1 \times 10^9$ cells of *Nannochloropsis oculata* strain NIES2145 were washed with 384 mM sorbitol solution to completely remove a salt, and the resultant was used as a host cell of transformation. The cassette for NoTE2 gene expression as amplified above was mixed by about 500 ng for each with the host cell, and electroporation was carried out under conditions of 50 µF, 500Ω and 2,200 v/2 mm.

After 24 hours recovery cultivation in f/2 liquid medium (75 mg of $NaNO_3$, 8 mg of $NaH_2PO_4.2H_2O$, 0.5 µg of vitamin B12, 0.5 µg of biotin, 100 µg of thiamine, 10 mg of $Na_2SiO_3.9H_2O$, 4.4 mg of $Na_2EDTA.2H_2O$, 3.16 mg of $FeCl_3.6H_2O$, 12 µg of $FeCl_3.6H_2O$, 21 µg of $ZnSO_4.7H_2O$, 180 µg of $MnCl_2.4H_2O$, 7 µg of $CuSO_4.5H_2O$, 7 µg of $Na_2MoO_4.2H_2O$/artificial sea water 1 L), the resultant material was inoculated in f/2 agar medium containing 2 µg/mL of zeocin, and cultured for two to three weeks under 12 h/12 h light-dark conditions at 25° C. under an atmosphere of 0.3% $CO_2$. A transformant containing the cassette for NoTE2 gene expression was selected from the resultant colonies by a PCR method.

(4) Extraction of Lipid From Culture Fluid and Analysis of Fatty Acids Contained Therein The selected strain was inoculated to 20 mL of medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare seed culture fluid. Then, 2 mL of the seed culture fluid was inoculated to 18 mL of the N15P5 medium, and subjected to shaking culture for one week under the 12 h/12 h light-dark conditions at 25° C. under the atmosphere of 0.3% $CO_2$, to prepare preculture fluid 1. Then, 2 mL of the preculture fluid 1 was inoculated to 18 mL of the N15P5 medium, and subjected to culture for one week under the 12 h/12 h light-dark conditions at 25° C. under the atmosphere of 0.3% $CO_2$, to prepare preculture fluid 2. Then, 2 mL of the preculture fluid 2 was inoculated to 18 mL of seawater medium (Daigo artificial seawater SP, manufactured by Wako Pure Chemical Industries), and subjected to shaking culture for twelve days under the 12 h/12 h light-dark conditions at 25° C. under the atmosphere of 0.3% $CO_2$.

In addition, as a negative control, an experiment was also conducted on the wild type strain, *Nannochloropsis oculata* strain NIES2145 (WT).

The fatty acid methyl esters were identified and quantitatively determined according to a method similar to Example 1. Table 4 shows the results.

Herein, in Table 4 below, "n" designates an integer of 0 to 5. For example, when "C18:n" is described, the description means a total of each fatty acid having compositions of C18:0, C18:1, C18:2, C18:3, C18:4 and C18.5.

Further, a total amount of fatty acids per turbidity of the culture fluid (TFA/OD660 nm) was calculated as well, and the results were shown in Table 4.

TABLE 4

(n = 3, Mean ± Standard Deviation)

| Introduced DNA | Fatty acid composition (% TFA) | | | | | | Contents of C14 fatty acid (mg/L) | TFA (mg/L) | TFA/OD660 nm |
|---|---|---|---|---|---|---|---|---|---|
| | C12:0 | C14:0 | C16:1 | C16:0 | C18:n | C20:n | | | |
| WT | 0.0 ± 0.0 | 3.4 ± 0.1 | 33.3 ± 0.2 | 37.4 ± 0.1 | 22.1 ± 0.2 | 3.8 ± 0.1 | 15.9 ± 0.2 | 471.3 ± 8.8 | 767.0 ± 16.1 |
| NoTE2-Nanno | 0.5 ± 0.0 | 4.9 ± 0.1 | 32.8 ± 0.0 | 35.7 ± 0.1 | 22.3 ± 0.2 | 3.7 ± 0.1 | 23.5 ± 0.7 | 476.1 ± 17.6 | 915.1 ± 33.1 |
| NoTE2_74-Nanno | 0.7 ± 0.0 | 5.3 ± 0.0 | 32.1 ± 0.1 | 34.3 ± 0.1 | 23.4 ± 0.2 | 4.2 ± 0.1 | 24.6 ± 0.4 | 467.3 ± 9.4 | 819.4 ± 14.3 |

Turbidity (OD660 nm) of the culture fluid was measured, and then extraction of lipids and analysis of fatty acids contained therein were performed as shown below.

To 1 mL of the culture fluid, 50 μL of 1 mg/mL 7-pentadecanone (methanol solution) as an internal standard was added, and then 0.5 mL of chloroform and 1 mL of methanol were further added thereto. The mixture was vigorously stirred and then was left for 10 minutes. Further, 0.5 mL of chloroform and 0.5 mL of 1.5% KCl were added thereto. The mixture was stirred and centrifuged for 5 minutes at 3,000 rpm, and then the chloroform layer (lower layer) was collected with pasteur pipette.

A nitrogen gas was blown onto the resultant chloroform layer to be dried into solid, 0.7 mL of 0.5 N potassium hydroxide/methanol solution was added thereto, and the resultant mixture was kept warm at 80° C. for 30 minutes. Then, 1 mL of 14% methanol solution of boron trifluoride (manufactured by Sigma-Aldrich) was added to the sample, and the mixture was kept warm at 80° C. for 10 minutes. Thereafter, 0.5 mL of hexane and 1 mL of saturated saline were added thereto, and the mixture was vigorously stirred and then was left for 10 minutes at room temperature. Then, the hexane layer (upper layer) was collected to obtain fatty acid methyl esters.

Under the measuring conditions as follows, the obtained fatty acid methyl esters were provided for gas chromatographic analysts.

<Gas Chromatography Conditions>
Analysis apparatus: 7890A (manufactured by Agilent Technologies)
Capillary column: DB-1 MS (30 m×200 μm×0.25 μm, manufactured by J&W Scientific)
Mobile phase: high purity helium
Oven temperature: maintained for 0.5 min. at 150° C.→150° C. to 220° C. (temperature increase at 40° C./min)→220° C. to 320° C. (temperature increase at 20° C./min)→maintained for 2 min, at 320° C. (post run 2 min.)
Injection port temperature: 300° C.
Injection method: split injection (split ratio: 75:1)
Amount of injection: 1 μL
Cleaning vial: methanol/chloroform
Detection method: FID
Detector temperature: 300° C.

As shown in Table 4, in the transformant having the introduced NoTE2 gene ("NoTE2-Nanno" in Table 4), a ratio of each of the C12:0 and C14:0 fatty acids significantly increased and productivity of these fatty acids increased in comparison with the wild type strain ("WT" in Table 4). Further, in this transformant, the total amount of fatty acids per turbidity of the culture fluid (TFA/OD660 nm) increased in comparison with the wild type strain, and it was suggested that productivity of fatty acids per cell was improved.

Further, also in the transformant having the introduced NoTE2_74 gene ("NoTE2_74-Nanno" in Table 4), a ratio of each of the C12:0 and C14:0 fatty acids significantly increased and productivity of these fatty acids increased in comparison with the wild type strain. Further, also in this transformant, the total amount of fatty acids per turbidity of the culture fluid increased in comparison with the wild type strain, and it was suggested that productivity of fatty acids per cell was improved. From this result, it was found that the amino acids of the 1st to 73rd positions of the amino acid sequence set forth in SEQ ID NO: 1 was not essential to the enzyme activity in the amino acid sequence set forth m SEQ ID NO: 1. Furthermore, it was suggested that a chloroplast transit signal sequence essential to localization in a chloroplast existed m the N-terminal side of the amino acid sequence set forth in SEQ ID NO: 1.

As described above, the transformant in which productivity of the medium chain fatty acids and productivity of the total fatty acids to be produced are improved can be prepared by promoting the expression of the acyl-ACP thioesterase gene as specified in the present invention. Further, productivity of the medium chain fatty acids can be improved by culturing this transformant.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2014-231355 filed in Japan on Nov. 14, 2014, which is entirely herein incorporated by reference.

What is claimed is:

1. A method of producing a lipid, comprising the steps of:
culturing a transformed host cell into which a gene encoding any one of the following proteins (A) to (C) has been introduced, and collecting the lipid from the cultured product:
(A) a protein consisting of the amino acid sequence of the $91^{st}$ to $348^{th}$ positions set forth in SEQ ID NO: 1;
(B) a protein consisting of an amino acid sequence having 90% or more identity with the amino acid sequence of the $91^{st}$ to $348^{th}$ positions set forth in SEQ ID NO: 1, and having acyl-ACP thioesterase activity; and
(C) a protein comprising an amino acid sequence that has 90% or more identity with the amino acid sequence of the $91^{st}$ to $348^{th}$ positions set forth in SEQ ID NO: 1, and having acyl-ACP thioesterase activity.

2. A method of modifying the composition of a lipid, comprising the steps of:
introducing a gene encoding any one of the following proteins (A) to (C) into a host, thereby obtaining a transformed host cell, and culturing the transformed host cell,
wherein the culturing enhances production of medium chain fatty acids or lipid containing medium chain fatty acids in the transformed host cell, thus modifying the transformed host cell's lipid composition as compared to that of the host into which the gene was not introduced;
(A) a protein consisting of the amino acid sequence of the $91^{st}$ to $348^{th}$ positions set forth in SEQ ID NO: 1;
(B) a protein consisting of an amino acid sequence having 90% or more identity with the amino acid sequence of the $91^{st}$ to $348^{th}$ positions set forth in SEQ ID NO: 1, and having acyl-ACP thioesterase activity; and
(C) a protein comprising an amino acid sequence that has 90% or more identity with the amino acid sequence of the $91^{st}$ to $348^{th}$ positions set forth in SEQ ID NO:1, and having acyl-ACP thioesterase activity.

3. The method according to claim 1, wherein the protein is protein (C) and protein (C) is any one of the following proteins (C1) to (C7):
(C1) a protein consisting of the amino acid sequence of the $1^{st}$ to $348^{th}$ positions set forth in SEQ ID NO: 1;
(C2) a protein consisting of the amino acid sequence of the $61^{st}$ to $348^{th}$ positions set forth in SEQ ID NO: 1;
(C3) a protein consisting of the amino acid sequence of the $71^{st}$ to $348^{th}$ positions set forth in SEQ ID NO: 1;
(C4) a protein consisting of the amino acid sequence of the $74^{th}$ to $348^{th}$ positions set forth in SEQ ID NO: 1;
(C5) a protein consisting of the amino acid sequence of the $81^{st}$ to $348^{th}$ positions set forth in SEQ ID NO: 1;
(C6) a protein consisting of an amino acid sequence having 90% or more identity with the amino acid sequence of any one of
the amino acid sequence of the $1^{st}$ to $348^{th}$ positions set forth in SEQ ID NO: 1;
the amino acid sequence of the $61^{st}$ to $348^{th}$ positions set forth in SEQ ID NO: 1;
the amino acid sequence of the $71^{st}$ to $348^{th}$ positions set forth in SEQ ID NO: 1;
the amino acid sequence of the $74^{th}$ to $348^{th}$ positions set forth in SEQ ID NO: 1; or
the amino acid sequence of the $81^{st}$ to $348^{th}$ positions set forth in SEQ ID NO: 1; and
having acyl-ACP thioesterase activity; and
(C7) a protein consisting of an amino acid sequence in which 1 to 20 amino acids are deleted, substituted, inserted or added to the amino acid sequence of any one of
the amino acid sequence of the $1^{st}$ to $348^{th}$ positions set forth in SEQ ID NO: 1;
the amino acid sequence of the $61^{st}$ to $348^{th}$ positions set forth in SEQ ID NO: 1;

the amino acid sequence of the 71st to 348th positions set forth in SEQ ID NO: 1:
the amino acid sequence of the 74th to 348th positions set forth in SEQ ID NO: 1: or the amino acid sequence of the 81st to 348th positions set forth in SEQ ID NO: 1: and
having acyl-ACP thioesterase activity.

4. The method according to claim 2, wherein the protein is protein (C) and protein (C) is any one of the following proteins (C1) to (C7):
(C1) a protein consisting of the amino acid sequence of the 1st to 348th positions set forth in SEQ ID NO: 1;
(C2) a protein consisting of the amino acid sequence of the 61st to 348th positions set forth in SEQ ID NO: 1;
(C3) a protein consisting of the amino acid sequence of the 71st to 348th positions set forth in SEQ ID NO: 1;
(C4) a protein consisting of the amino acid sequence of the 74th to 348th positions set forth in SEQ ID NO: 1;
(C5) a protein consisting of the amino acid sequence of the 81st to 348th positions set forth in SEQ ID NO: 1;
(C6) a protein consisting of an amino acid sequence having 90% or more identity with the amino acid sequence of any one of
the amino acid sequence of the 1st to 348th positions set forth in SEQ ID NO: 1;
the amino acid sequence of the 61st to 348th positions set forth in SEQ ID NO: 1;
the amino acid sequence of the 71st to 348th positions set forth in SEQ ID NO: 1;
the amino acid sequence of the 74th to 348th positions set forth in SEQ ID NO: 1; or
the amino acid sequence of the 81st to 348th positions set forth in SEQ ID NO: 1;
and having acyl-ACP thioesterase activity; and
(C7) a protein consisting of an amino acid sequence in which 1 to 20 amino acids are deleted, substituted, inserted or added to the amino acid sequence of any one of
the amino acid sequence of the 1st to 348th positions set forth in SEQ ID NO: 1:
the amino acid sequence of the 61st to 348th positions set forth in SEQ ID NO: 1:
the amino acid sequence of the 71st to 348th positions set forth in SEQ ID NO: 1:
the amino acid sequence of the 74th to 348th positions set forth in SEQ ID NO: 1; or
the amino acid sequence of the 81st to 348th positions set forth in SEQ ID NO: 1; and
having acyl-ACP thioesterase activity.

5. The method according to claim 1, wherein the host is *Escherichia coli*.

6. The method according to claim 2, wherein the host is *Escherichia coli*.

7. The method according to claim 1, wherein the host is a microalga.

8. The method according to claim 7, wherein the microalga is an alga belonging to the genus *Nannochloropsis*.

9. The method according to claim 1, wherein the lipid contains a fatty acid having 14 carbon atoms or a fatty acid ester compound thereof.

10. The method according to claim 2, wherein the host is a microalga.

11. The method according to claim 10, wherein the microalga is an alga belonging to the genus *Nannochloropsis*.

12. The method according to claim 2, wherein the lipid contains a fatty acid having 14 carbon atoms or a fatty acid ester compound thereof.

13. A transformed host cell which is obtained by introducing a gene encoding any one of the following proteins (A) to (C) into a host cell:
(A) a protein consisting of the amino acid sequence of the 91st to 348th positions set forth in SEQ ID NO: 1;
(B) a protein consisting of an amino acid sequence having 90% or more identity with the amino acid sequence of the 91st to 348th positions set forth in SEQ ID NO: 1, and having acyl-ACP thioesterase activity; and
(C) a protein comprising an amino acid sequence that has 90% or more identity with the amino acid sequence of the 91st to 348th positions set forth in SEQ ID NO:1, and having acyl-ACP thioesterase activity.

14. The transformed host cell transformant according to claim 13, wherein the protein is protein (C) and protein (C1 is any one of the following proteins (C1) to (C7)
(C1) a protein consisting of the amino acid sequence of the 1st to 348th positions set forth in SEQ ID NO: 1;
(C2) a protein consisting of the amino acid sequence of the 61st to 348th positions set forth in SEQ ID NO: 1;
(C3) a protein consisting of the amino acid sequence of the 71st to 348th positions set forth in SEQ ID NO: 1;
(C4) a protein consisting of the amino acid sequence of the 74th to 348th positions set forth in SEQ ID NO: 1;
(C5) a protein consisting of the amino acid sequence of the 81st to 348th positions set forth in SEQ ID NO: 1;
(C6) a protein consisting of an amino acid sequence having 90% or more identity with the amino acid sequence of any one of
the amino acid sequence of the 1st to 348th positions set forth in SEQ ID NO: 1;
the amino acid sequence of the 61st to 348th positions set forth in SEQ ID NO: 1;
the amino acid sequence of the 71st to 348th positions set forth in SEQ ID NO: 1;
the amino acid sequence of the 74th to 348th positions set forth in SEQ ID NO: 1; or
the amino acid sequence of the 81st to 348th positions set forth in SEQ ID NO: 1 and having acyl-ACP thioesterase activity; and
(C7) a protein consisting of an amino acid sequence in which 1 to 20 amino acids are deleted, substituted, inserted or added to the amino acid sequence of any one of
the amino acid sequence of the 1st to 348th positions set forth in SEQ ID NO: 1;
the amino acid sequence of the 61st to 348th positions set forth in SEQ ID NO: 1;
the amino acid sequence of the 71st to 348th positions set forth in SEQ ID NO: 1;
the amino acid sequence of the 74th to 348th positions set forth in SEQ ID NO: 1; or
the amino acid sequence of the 81st to 348th positions set forth in SEQ ID NO: 1;
and having acyl-ACP thioesterase activity.

15. The transformed host cell according to claim 13, wherein the host is *Escherichia coli*.

16. The transformed host cell according to claim 13, wherein the host is a microalga.

17. The transformed host cell according to claim 16, wherein the microalga is an alga belonging to the genus *Nannochloropsis*.

18. The method of claim 1, wherein the protein is protein (C) and protein (C) comprises the amino acid sequence of the 91st to 348th positions set forth in SEQ ID NO:1 and has acyl-ACP thioesterase activity.

19. The method of claim 2, wherein the protein is protein (C) and protein (C) comprises the amino acid sequence of the 91$^{st}$ to 348$^{th}$ positions set forth in SEQ ID NO:1 and has acyl-ACP thioesterase activity.

20. The transformed host cell of claim 13, wherein the protein is protein (C) and protein (C) comprises the amino acid sequence of the 91$^{st}$ to 348$^{th}$ positions set forth in SEQ ID NO:1 and has acyl-ACP thioesterase activity.

* * * * *

SEQUENCE LISTING

<160> NUMBER OF SEQ ID NOS: 37

<210> SEQ ID NO 1
<211> LENGTH: 348
<212> TYPE: PRT
<213> ORGANISM: Nannochloropsis oculata

<400> SEQUENCE: 1

```
Met Arg Ile Pro Ser Leu Ile Leu Cys Phe Ala Phe Leu Ala Ser Ala
1               5                   10                  15

Pro Ala Val Ala Phe Leu Leu Pro Pro Leu Pro Cys Phe Ser Ser Ser
            20                  25                  30

Leu Gln Thr Val Thr Asn Thr Ile Thr Thr Ser Ser Arg Phe Ser Ser
        35                  40                  45

Ser Ser Ser Ser Ser Ser Ser Ser Ser Ser Ser Ser Arg Pro Arg
    50                  55                  60

Cys Ser Pro Leu Leu Ser Val Thr Thr Ala Ala Thr Ala Ser Ser Ala
65                  70                  75                  80

Thr Glu Glu Ala Glu Asn Pro Ser Leu Thr Gln Gly Val Phe Ile Glu
                85                  90                  95

His Thr Asp Arg Tyr Gly Met Val Tyr His Ser Asn Tyr Leu Leu Phe
            100                 105                 110

Leu Cys Arg Ala Leu His Leu Thr Leu Gly Arg His Val Val Thr Arg
        115                 120                 125

Leu Asp Asn Phe Arg Phe Lys Ala Ser Ala Arg Leu Gly His Asp Ile
    130                 135                 140

Ala Ile Asp Val Arg Pro Lys Ala Gly Lys Asp Asn Thr Phe Val Thr
145                 150                 155                 160

Ser Ile Lys Glu Ser Glu Thr Pro His Thr Thr Phe Ile Thr Ala Asp
                165                 170                 175

Val Ser Ala Phe Pro Leu Pro Glu Arg Gly Arg Glu Gly Gly Arg Glu
            180                 185                 190

Asp Trp Ala Ala Tyr Thr Ile Ser Glu Glu Ala Leu Arg Lys Val
        195                 200                 205

Val Ala Ser Pro Asp Lys Val Met Glu Ala Val Leu Trp Thr Asp Glu
    210                 215                 220

Leu Gly Val His Gly Leu Leu Thr Pro His Ala Val Leu Ser Leu Phe
225                 230                 235                 240

Glu Arg Gly Arg Ser Asp Ser Leu Gly Gly Pro Asp Arg Leu Glu Glu
                245                 250                 255

Leu Met Asp Asp Gly Tyr Met Phe Val Val Ala Arg Ile Asp Gly Tyr
            260                 265                 270

Arg Phe Asp Pro Ser Leu Arg Leu Glu Glu Gly Glu Ala Leu Gln Val
        275                 280                 285

Leu Gly Arg Phe Lys Pro Lys Ser Asp Ala Ile Val Val Cys Glu Gln
    290                 295                 300

Val Leu Ile Val Lys Ala Thr Gln Gln Ile Val Ala Gln Ala Leu Val
305                 310                 315                 320

Thr Leu Ala Cys Ile Gly Ala Val Asp Gly Lys Leu Arg Gly Val Pro
                325                 330                 335

Ser Lys Ala Leu Glu Ser Met Asn Met Gly Thr Thr
            340                 345
```

<210> SEQ ID NO 2
<211> LENGTH: 1047

<212> TYPE: DNA
<213> ORGANISM: Nannochloropsis oculata

<400> SEQUENCE: 2

```
atgagaatac cttcccttat cctttgcttc gcatttctag cgagcgctcc cgctgttgcc      60
ttcctgctgc cgccgctgcc ttgcttctct tcttcgcttc agacagtcac caacacaatc     120
acgacaagca gtcgcttcag cagcagcagc agcagcagca gcagcagcag cagcagcagc     180
agcagaccaa gatgcagccc cttgttatcc gtcacgactg ccgctactgc ttcatctgcg     240
acagaggaag cggaaaaccc gagcttgact caaggagtat tcatcgagca taccgacagg     300
tacgggatgg tctaccactc caactacctg ctcttcctct gtcgcgctct ccacctcacc     360
ctgggccggc acgtggtgac acgcctagat aactttcggt tcaaagcatc ggctcgcctg     420
ggccacgata tcgccatcga cgtgaggccc aaggcgggga agacaacac tttcgtcacc      480
agcatcaagg aaagcgaaac tcctcacact acctttatca ccgcggacgt atcggccttc     540
cccttcctg agcgaggaag ggagggagga agggaggatt gggctgcata tacgatctcg     600
gaggaagagg cattgaggaa ggtggtggcc tcccccgaca aggtcatgga ggccgttttg     660
tggaccgacg agctgggagt gcacggcctg ctcacaccgc atgccgtcct ttccctgttt     720
gagcggggaa ggagtgattc cctgggtggt ccggaccgcc tggaggagct catggatgac     780
ggctacatgt tcgtcgtcgc ccgcatcgac ggctaccgct tcgacccctc cctccgtctc     840
gaggagggag aggcccttca agtgctcggc cgatttaagc ccaagtccga cgccatcgtt     900
gtatgcgagc aggtcctcat cgtcaaggcc acccaacaga tcgtggctca ggccctcgtg     960
acgcttgcct gcatcggcgc cgtggatggc aaattgcgag gcgtgccttc caaggccctt    1020
gagagtatga acatgggcac gacgtag                                        1047
```

<210> SEQ ID NO 3
<211> LENGTH: 36
<212> TYPE: DNA
<213> ORGANISM: Artificial Sequence
<220> FEATURE:
<223> OTHER INFORMATION: PCR primer 1 for NoTE2

<400> SEQUENCE: 3

```
gcggccgctc tagagatgag aataccttcc cttatc                               36
```

<210> SEQ ID NO 4
<211> LENGTH: 36
<212> TYPE: DNA
<213> ORGANISM: Artificial Sequence
<220> FEATURE:
<223> OTHER INFORMATION: PCR primer 2 for NoTE2

<400> SEQUENCE: 4

```
acaaaatatt aacgcctacg tcgtgcccat gttcat                               36
```

<210> SEQ ID NO 5
<211> LENGTH: 20
<212> TYPE: DNA
<213> ORGANISM: Artificial Sequence
<220> FEATURE:
<223> OTHER INFORMATION: PCR primer 1 for pBluescriptII

<400> SEQUENCE: 5

```
ctctagagcg gccgccaccg                                                 20
```

<210> SEQ ID NO 6

```
<211> LENGTH: 24
<212> TYPE: DNA
<213> ORGANISM: Artificial Sequence
<220> FEATURE:
<223> OTHER INFORMATION: PCR primer 2 for pBluescriptII

<400> SEQUENCE: 6
gcgttaatat tttgttaaaa ttcg                                              24

<210> SEQ ID NO 7
<211> LENGTH: 35
<212> TYPE: DNA
<213> ORGANISM: Artificial Sequence
<220> FEATURE:
<223> OTHER INFORMATION: PCR primer 1 for NoTE2_61

<400> SEQUENCE: 7
gcggccgctc tagagagcag accaagatgc agccc                                  35

<210> SEQ ID NO 8
<211> LENGTH: 35
<212> TYPE: DNA
<213> ORGANISM: Artificial Sequence
<220> FEATURE:
<223> OTHER INFORMATION: PCR primer 1 for NoTE2_71

<400> SEQUENCE: 8
gcggccgctc tagaggtcac gactgccgct actgc                                  35

<210> SEQ ID NO 9
<211> LENGTH: 35
<212> TYPE: DNA
<213> ORGANISM: Artificial Sequence
<220> FEATURE:
<223> OTHER INFORMATION: PCR primer 1 for NoTE2_74

<400> SEQUENCE: 9
gcggccgctc tagaggccgc tactgcttca tctgc                                  35

<210> SEQ ID NO 10
<211> LENGTH: 35
<212> TYPE: DNA
<213> ORGANISM: Artificial Sequence
<220> FEATURE:
<223> OTHER INFORMATION: PCR primer 1 for NoTE2_81

<400> SEQUENCE: 10
gcggccgctc tagagacaga ggaagcggaa aaccc                                  35

<210> SEQ ID NO 11
<211> LENGTH: 35
<212> TYPE: DNA
<213> ORGANISM: Artificial Sequence
<220> FEATURE:
<223> OTHER INFORMATION: PCR primer 1 for NoTE2_91

<400> SEQUENCE: 11
gcggccgctc tagagcaagg agtattcatc gagca                                  35

<210> SEQ ID NO 12
<211> LENGTH: 35
<212> TYPE: DNA
<213> ORGANISM: Artificial Sequence
<220> FEATURE:
<223> OTHER INFORMATION: PCR primer 1 for NoTE2_101

<400> SEQUENCE: 12
```

```
gcggccgctc tagagtacgg gatggtctac cactc                                35
```

<210> SEQ ID NO 13
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 13

```
atggccaagc tgaccagcgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300
ccgtgggggc gggagttcgc cctgcgcgac cggccggca actgcgtgca cttcgtggcc     360
gaggagcagg actaa                                                     375
```

<210> SEQ ID NO 14
<211> LENGTH: 500
<212> TYPE: DNA
<213> ORGANISM: Artificial Sequence
<220> FEATURE:
<223> OTHER INFORMATION: Tubulin promoter

<400> SEQUENCE: 14

```
actgcgcatg gattgaccga cggccggttg ccaactttg gggtcggccc ccctttcta      60
gcccttgccc gtccagcaat taaaaattat caacggcata ccggcactgg aagcttcggg    120
tttacaattt tggcttgcct tcctaatact gtaccgcgga gaacgtatga tattacagaa    180
aaatgccttg cacagttagc gcaaagggaa aacgtttctc cgccattgta cttttttggaa   240
gagggaaagc gattgtaaaa tatggctctc cgctacgaga gtttgggctg ttgatacatg    300
tgaaaataag tgtggacgac tttgaatgac ttgatcaggc tgtttgcaca taaccagc     360
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt ttgtgaagca                                                500
```

<210> SEQ ID NO 15
<211> LENGTH: 37
<212> TYPE: DNA
<213> ORGANISM: Artificial Sequence
<220> FEATURE:
<223> OTHER INFORMATION: PCR primer No. 15

<400> SEQUENCE: 15

```
cttttttgtg aagcaatggc caagttgacc agtgccg                             37
```

<210> SEQ ID NO 16
<211> LENGTH: 36
<212> TYPE: DNA
<213> ORGANISM: Artificial Sequence
<220> FEATURE:
<223> OTHER INFORMATION: PCR primer No. 16

<400> SEQUENCE: 16

```
tttcccccat cccgattagt cctgctcctc ggccac                              36
```

<210> SEQ ID NO 17
<211> LENGTH: 35
<212> TYPE: DNA
<213> ORGANISM: Artificial Sequence
<220> FEATURE:
<223> OTHER INFORMATION: PCR primer No. 17

<400> SEQUENCE: 17
cgagctcggt acccgactgc gcatggattg accga         35

<210> SEQ ID NO 18
<211> LENGTH: 28
<212> TYPE: DNA
<213> ORGANISM: Artificial Sequence
<220> FEATURE:
<223> OTHER INFORMATION: PCR primer No. 18

<400> SEQUENCE: 18
tgcttcacaa aaaagacagc ttcttgat         28

<210> SEQ ID NO 19
<211> LENGTH: 25
<212> TYPE: DNA
<213> ORGANISM: Artificial Sequence
<220> FEATURE:
<223> OTHER INFORMATION: PCR primer No. 19

<400> SEQUENCE: 19
tcgggatggg ggaaaaaaac ctctg         25

<210> SEQ ID NO 20
<211> LENGTH: 36
<212> TYPE: DNA
<213> ORGANISM: Artificial Sequence
<220> FEATURE:
<223> OTHER INFORMATION: PCR primer No. 20

<400> SEQUENCE: 20
actctagagg atcccctttc gtaaataaat cagctc         36

<210> SEQ ID NO 21
<211> LENGTH: 1000
<212> TYPE: DNA
<213> ORGANISM: Nannochloropsis oculata

<400> SEQUENCE: 21
tcgggatggg ggaaaaaaac ctctgtgtgg gctgtcagtt gatactatta gaggtctttt         60
gttttgtttg tggctgcgtg tgtgtgtttg catgagaaat agacttgaga atatcggaag        120
gaactttgac atggtaaacg aggaaaagaa aatcttcaaa aaggaataat gggtaaaaac        180
aaggagcacc gggtctcttt agaaatgctt ctcggcggaa aaccagaaaa aaaggtagaa        240
tatgtcgact ttttcgctta tcattataga atgaaagatc gaatggccaa gggatttata        300
aattctttct ttatgttgtc gtagaactta ctttccatcc cgagggaggt gtatgcaggc        360
caaaccctct gacatgggcg caatatctct atgaaaggtt gttggaatac attgtccgac        420
ctccttcgag gcggagccgc atagttgaag ataggtgct tgcttcatcc atctcatgac        480
gctttgccag tgactcactc atgcatgtga cacatttagt tctgctcgct caagcctggc        540
ccctcctgac atgcacacat tgcacttgta ggtgggccac gtttagtata gacgccaccc        600
ctgtcgcacc atcggtccca gagcaggagc acgcttccct actcctgtac gctccccctg        660
cttccccccc tgctcgtcaa cgatggcgac gccagcggct gcgaattaca gtgacggcgc        720

```
ggccgctcag gatgacagct cctctccttc aacatctccc aatcttccac ccccgcccat    780
gtcgtcgttc gtacggccta tgctgaccga tatgtaccaa attacaatgg tcttcgcgta    840
ctggaagcaa aagcggcacc aggacagggc catctttgag ctcttttcc ggaagacacc     900 ctttaaggga gagtttgcca ttatggccgg cattgacgaa gtactcaagt acttggccca    960
ctttcgcttc tccgaggagg agctgattta tttacgaaag                          1000
```

<210> SEQ ID NO 22
<211> LENGTH: 20
<212> TYPE: DNA
<213> ORGANISM: Artificial Sequence
<220> FEATURE:
<223> OTHER INFORMATION: PCR primer No. 22

<400> SEQUENCE: 22

```
gggatcctct agagtcgacc                                                20
```

<210> SEQ ID NO 23
<211> LENGTH: 20
<212> TYPE: DNA
<213> ORGANISM: Artificial Sequence
<220> FEATURE:
<223> OTHER INFORMATION: PCR primer No. 23

<400> SEQUENCE: 23

```
cgggtaccga gctcgaattc                                                20
```

<210> SEQ ID NO 24
<211> LENGTH: 37
<212> TYPE: DNA
<213> ORGANISM: Artificial Sequence
<220> FEATURE:
<223> OTHER INFORMATION: PCR primer No. 24

<400> SEQUENCE: 24

```
cagcccgcat caacaatgag aataccttcc cttatcc                             37
```

<210> SEQ ID NO 25
<211> LENGTH: 35
<212> TYPE: DNA
<213> ORGANISM: Artificial Sequence
<220> FEATURE:
<223> OTHER INFORMATION: PCR primer No. 25

<400> SEQUENCE: 25

```
ctcttccaca gaagcctacg tcgtgcccat gttca                               35
```

<210> SEQ ID NO 26
<211> LENGTH: 35
<212> TYPE: DNA
<213> ORGANISM: Artificial Sequence
<220> FEATURE:
<223> OTHER INFORMATION: PCR primer No. 26

<400> SEQUENCE: 26

```
cgagctcggt acccgttctt ccgcttgttg ctgcc                               35
```

<210> SEQ ID NO 27
<211> LENGTH: 25
<212> TYPE: DNA
<213> ORGANISM: Artificial Sequence
<220> FEATURE:
<223> OTHER INFORMATION: PCR primer No. 27

<400> SEQUENCE: 27
tgttgatgcg ggctgagatt ggtgg                                    25

<210> SEQ ID NO 28
<211> LENGTH: 21
<212> TYPE: DNA
<213> ORGANISM: Artificial Sequence
<220> FEATURE:
<223> OTHER INFORMATION: PCR primer No. 28

<400> SEQUENCE: 28
gcttctgtgg aagagccagt g                                        21

<210> SEQ ID NO 29
<211> LENGTH: 28
<212> TYPE: DNA
<213> ORGANISM: Artificial Sequence
<220> FEATURE:
<223> OTHER INFORMATION: PCR primer No. 29

<400> SEQUENCE: 29
ggcaagaaaa gctgggggaa aagacagg                                 28

<210> SEQ ID NO 30
<211> LENGTH: 800
<212> TYPE: DNA
<213> ORGANISM: Nannochloropsis oculata

<400> SEQUENCE: 30
ttcttccgct tgttgctgcc gatggcggcc atggtctcta agatggagtg gatggaggag    60
gaggcgagcg tagcagcaag cgtgagttat acagccaggc acatgtcgca atccttcggt   120
ctcgggctta aaatccacgc actaatcacg ctgggccatg caaagagcaa tgccgaggcc   180
caccacacaa aacgctgtgt cgcgcgttgc ggcctgaagc ttcatacttc ttagtcgccg   240
ccaaaagggc tcgagagacg agacccgttg gcatgaccga tgttgttcga cgcggtttgc   300
ttcgtcacag tcgacgtgat tcaggaatct ggagcctgca gatcattttt ttcagcctga   360
tatcgttctt ttccactgag aaccatcaga ccacctttc ttccattgtg tgaaggagta    420
ggagttgccg tgctgctttg tgggagacat ctgcgatggt gaccagcctc ccgtcgtctg   480
gtcgacgtga cgagcctctt cactgttctt cgacggagag acgcaagcga dacggctcta   540
gaccttttgg acacgcattc tgtgtgtgaa ctagtggaca gtgataccac gtctgaaagc   600
tcaccactgc ccatggtgca gctacttgtc acaaagtttt gactccgtcg gtatcaccat   660
tcgcgctcgt gtgcctggtt gttccgccac gccggcctgc cccggggcgg ggcaatattc   720
taaaatctca cgcaaaacac cgcacttacc cctcacacat attcgtgata gaccaccacc   780
aatctcagcc cgcatcaaca                                              800

<210> SEQ ID NO 31
<211> LENGTH: 613
<212> TYPE: DNA
<213> ORGANISM: Nannochloropsis oculata

<400> SEQUENCE: 31
gcttctgtgg aagagccagt ggtagtagca gtagcagcag cagtagcagc cgcagcactc    60
agtgttggcg cgagagattg tccatcccctt cttaacctac cggaagagaa ataaggcctt   120
tctcccgtag ctgtcttcgt ttgtttgtgc tgattgcttg atatgagagt gttgaattcc   180
tgcatcatgt tttctctgt agtccttttcc taccccgtc attttctttt ctccctggtt    240

```
cttcttttgt caccottatt ttacataaaa ttttctttgt ttatagtgag aggaaggtag      300 agagggaaa acaagaacaa cgaacgcaag cgtgtgaaag gagggcgagt agaagagaaa       360
cagatctgtt gagcattgag agtggagccg ggggaaaggc ttgtgtgttg tctttgaaaa      420
agttgtttaa atcacgaatc cgttagttct catgtgtacc tctttcacta catgtgatgg      480
agaaaacaaa agtgtgagga ttaattgaag aaaaagaaga gttcgacacg tcaaaccgcc      540
caaaagacgt cacaaagaga acttgattct ctttgccgtg ttgatcctgt ctttccccc      600 agcttttctt gcc                                                         613
```

<210> SEQ ID NO 32
<211> LENGTH: 35
<212> TYPE: DNA
<213> ORGANISM: Artificial Sequence
<220> FEATURE:
<223> OTHER INFORMATION: PCR primer No. 32

<400> SEQUENCE: 32

```
ccagcttttc ttgccactgc gcatggattg accga                                 35
```

<210> SEQ ID NO 33
<211> LENGTH: 35
<212> TYPE: DNA
<213> ORGANISM: Artificial Sequence
<220> FEATURE:
<223> OTHER INFORMATION: PCR primer No. 33

<400> SEQUENCE: 33

```
cgcggtgttg cgcgcgccgc tactgcttca tctgc                                 35
```

<210> SEQ ID NO 34
<211> LENGTH: 36
<212> TYPE: DNA
<213> ORGANISM: Artificial Sequence
<220> FEATURE:
<223> OTHER INFORMATION: PCR primer No. 34

<400> SEQUENCE: 34

```
cagcccgcat caacaatgaa gaccgccgct ctcctc                                36
```

<210> SEQ ID NO 35
<211> LENGTH: 28
<212> TYPE: DNA
<213> ORGANISM: Artificial Sequence
<220> FEATURE:
<223> OTHER INFORMATION: PCR primer No. 35

<400> SEQUENCE: 35

```
gcgcgcaaca ccgcgggtgc gggagaac                                         28
```

<210> SEQ ID NO 36
<211> LENGTH: 99
<212> TYPE: DNA
<213> ORGANISM: Nannochloropsis oculata

<400> SEQUENCE: 36

```
atgaagaccg ccgctctcct cactgtctcc accctcatgg gcgcccaggc ctttatggcc      60
cccgccccca agttctcccg cacccgcggt gttgcgcgc                             99
```

<210> SEQ ID NO 37
<211> LENGTH: 900
<212> TYPE: DNA

-continued

```
<213> ORGANISM: Nannochloropsis oculata

<400> SEQUENCE: 37
ttgctgccat gccggcagct gtagacgtta tgaagggcag acttgaggct actgccttat      60
gaagacggcg tccgtccagc atcttcccac ccagccatac ggcaagaata ggaacatcta     120
tccagccata cggcaagggt cagggatggg gcgcagtggt acggcaaggg cgtgtcgata     180
gttgtgcatg aagggtgag cgcagaaaaa cgacgccacc ttccccacag cgatacggcg      240
cgatagggcg attgttgggg catatgccca gtgggtcagg gaggggacca agccatacga     300
cgaggaattg tcgacaggct tcgctctcca gaccacctgt cgcgactgcg tcgcagattt     360
agcgccgtgt tatgtctata atctgttgtg tggtggaggg agaacacgca gaggcgcagc    420
tgctgaggtt cgtgccgagg gagattatcg ctcggctctg tcgtttgaag acctgccgcc    480
ttaaacgacg atgtggactc ggagaaacaa atggcaactt catgtaccgc aagccctgag    540
acagtgtttc tcagctgtcg tgtccggtct catctttcct tcgagctgag gccagagtcc    600
aatgtggggc acgaccagg cacaagaagg acaaacggga gcgatggacc gggcgagaaa    660
cgataactgg agtgcgcctc ggacggagag aaaaaggggg gcgacgagac catgtaccac    720
catatggcga cgtgatcctg tttccctttt ggctgggctg tgccatgagg ctcctcatca   780
cgtgccattc gtcagtcgtt gctcaataac ctccccgaca tagcgtattg gtgctcttac    840
ctccttttca ccctcctata cctactttca cataacccac acatttctcc actcaacagg   900
```